(12) United States Patent
Chiosa et al.

(10) Patent No.: US 11,514,200 B2
(45) Date of Patent: Nov. 29, 2022

(54) MODELING A PATIENT-INDIVIDUALISED DENTURE PART

(71) Applicant: EXOCAD GMBH, Darmstadt (DE)

(72) Inventors: Iurie Chiosa, Weiterstadt (DE); Maik Gerth, Darmstadt (DE); Tillmann Steinbrecher, Seeheim-Jugenheim (DE)

(73) Assignee: EXOCAD GMBH, Darmstadt (DE)

( * ) Notice: Subject to any disclaimer, the term of this patent is extended or adjusted under 35 U.S.C. 154(b) by 0 days.

(21) Appl. No.: 17/436,995

(22) PCT Filed: Mar. 3, 2020

(86) PCT No.: PCT/EP2020/055577
§ 371 (c)(1),
(2) Date: Sep. 7, 2021

(87) PCT Pub. No.: WO2020/182546
PCT Pub. Date: Sep. 17, 2020

(65) Prior Publication Data
US 2022/0180012 A1  Jun. 9, 2022

(30) Foreign Application Priority Data
Mar. 8, 2019  (EP) .................................... 19161770

(51) Int. Cl.
*G06F 30/10* (2020.01)
*A61C 13/01* (2006.01)
(Continued)

(52) U.S. Cl.
CPC .............. *G06F 30/10* (2020.01); *A61C 13/01* (2013.01); *A61C 13/34* (2013.01); *G06T 17/20* (2013.01);
(Continued)

(58) Field of Classification Search
CPC ......... G06F 30/10; A61C 13/01; A61C 13/34; G06T 17/20; G06T 19/20; G06T 2210/41
See application file for complete search history.

(56) References Cited

U.S. PATENT DOCUMENTS 6,664,986 B1 * 12/2003 Kopelman ........... A61C 9/0046
715/848
9,996,981 B1 * 6/2018 Tran ........................ G06T 19/20
(Continued)

FOREIGN PATENT DOCUMENTS

| DE | 102011005899 A1 | 3/2011 |
| EP | 2134290 A1 | 12/2009 |
| WO | 2008128700 A1 | 10/2008 |

OTHER PUBLICATIONS

International Search Report and Written Opinion dated May 18, 2020, issued in corresponding PCT Application No. PCT/EP2020/055577, filed Mar. 3, 2020, including English translation of the ISR.
(Continued)

*Primary Examiner* — Said Broome
(74) *Attorney, Agent, or Firm* — Perry + Currier, Inc.

(57) ABSTRACT

The invention relates to a method for modelling a patient-individualised denture part (140). The method comprises providing a digital three-dimensional patient situation model (118), a digital three-dimensional denture part model (114), and one or more geometric adaptation criteria defined using patient-specific delimiting surfaces. A denture part geometry of the denture part model is adapted in a patient-individualised manner to a patient situation geometry of the patient situation model. The patient-individualised adaptation process also comprises repeatedly interactively making user-defined changes to the denture part model, wherein the denture part model dynamically passes through a sequence of intermediate states during the course of each of the user-defined changes until a change state resulting from each
(Continued)

Figure 1:
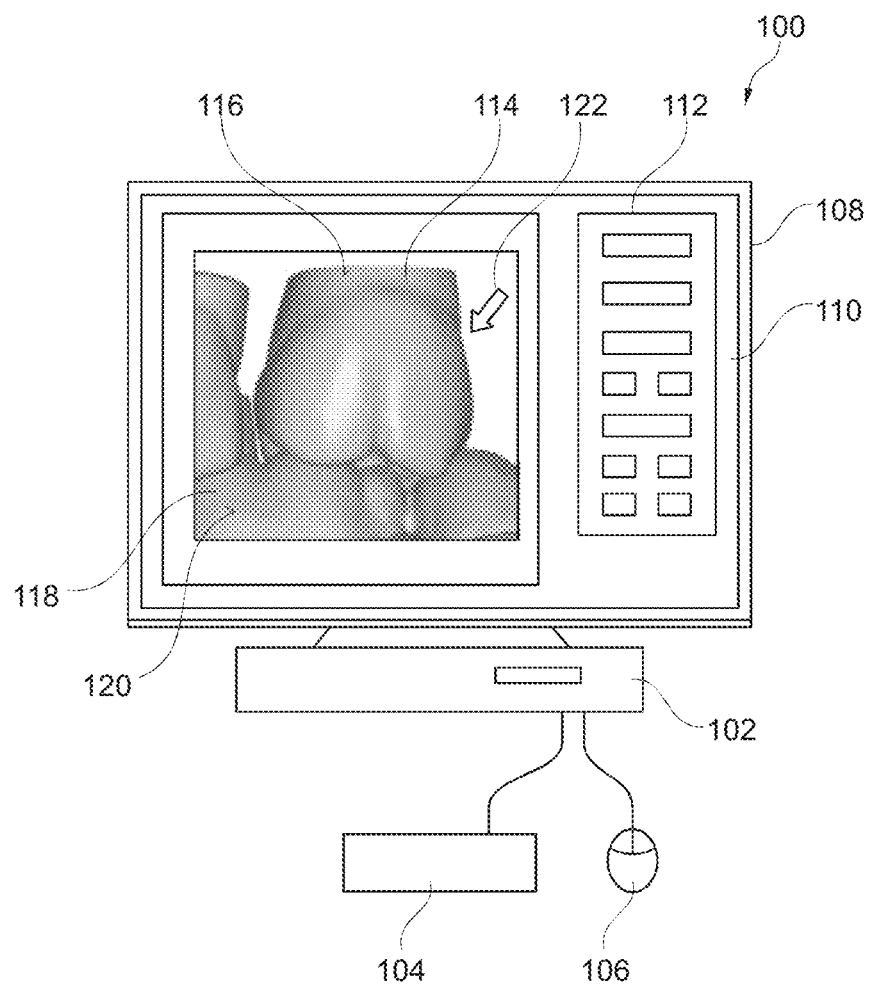

user-defined change is reached. The dynamic passing through of the relevant sequence of intermediate states until the corresponding change state has been reached is displayed on a display device (108) by means of a graphical user surface (119).

20 Claims, 14 Drawing Sheets

(51) Int. Cl.
*A61C 13/34* (2006.01)
*G06T 17/20* (2006.01)
*G06T 19/20* (2011.01)

(52) U.S. Cl.
CPC .......... *G06T 19/20* (2013.01); *G06T 2200/24* (2013.01); *G06T 2210/41* (2013.01); *G06T 2219/2004* (2013.01)

(56) References Cited

U.S. PATENT DOCUMENTS

| | | | | |
|---|---|---|---|---|
| 2005/0186540 | A1* | 8/2005 | Taub | G05B 19/0421 700/118 |
| 2008/0020350 | A1* | 1/2008 | Matov | G06T 17/20 433/213 |
| 2010/0009308 | A1* | 1/2010 | Wen | A61C 7/08 700/118 |
| 2010/0281370 | A1* | 11/2010 | Rohaly | G06F 3/04815 715/810 |
| 2012/0015316 | A1* | 1/2012 | Sachdeva | G06T 19/20 382/128 |
| 2013/0282351 | A1 | 10/2013 | Tank | |
| 2014/0162233 | A1* | 6/2014 | Hultgren | A61C 13/34 434/270 |
| 2015/0111177 | A1* | 4/2015 | Fisker | A61C 9/004 433/199.1 |
| 2015/0142400 | A1* | 5/2015 | Matov | G06T 17/20 345/420 |
| 2016/0008116 | A1* | 1/2016 | Glinec | G06T 19/20 433/29 |
| 2017/0178327 | A1* | 6/2017 | Somasundaram | A61B 5/4547 |
| 2018/0085203 | A1 | 3/2018 | Ramirez et al. | |

OTHER PUBLICATIONS

International Preliminary Report on Patentability, dated Jan. 21, 2021, issued in corresponding PCT Application No. PCT/EP2020/055577, filed Mar. 3, 2020, including English translation of the IPRP, including English Translation.

* cited by examiner

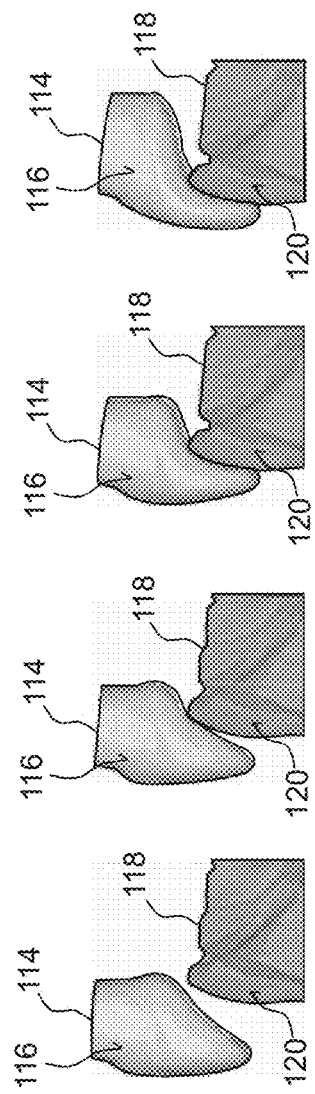
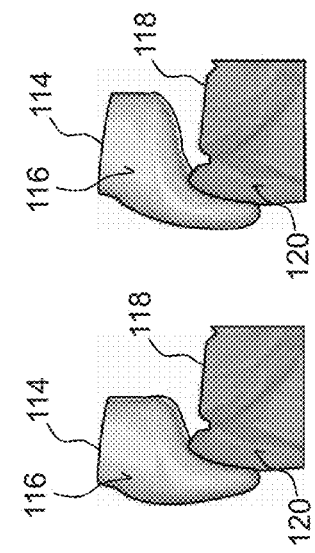
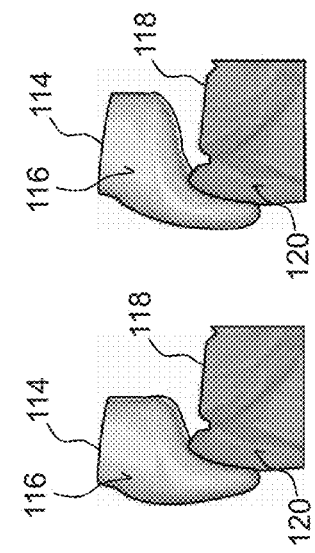
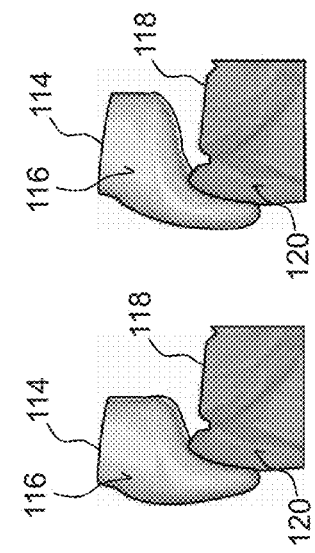
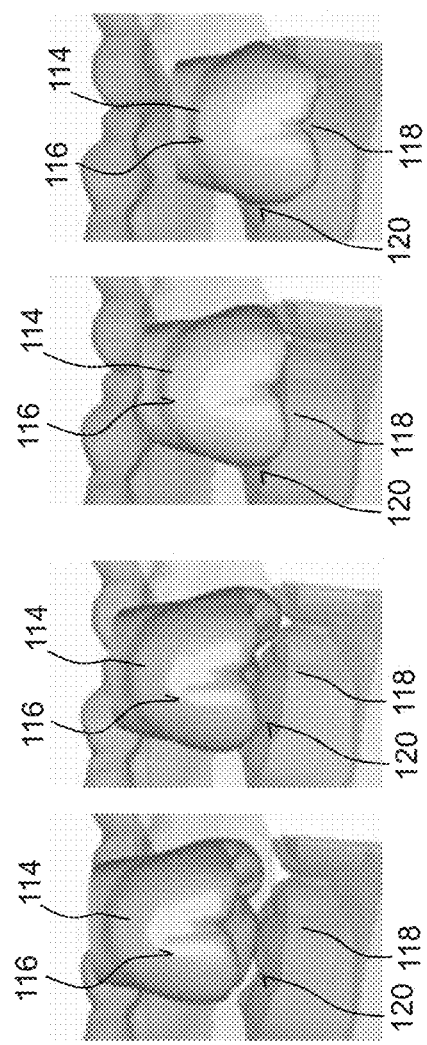
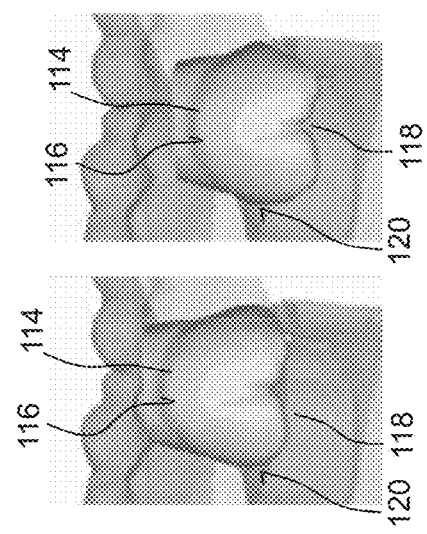
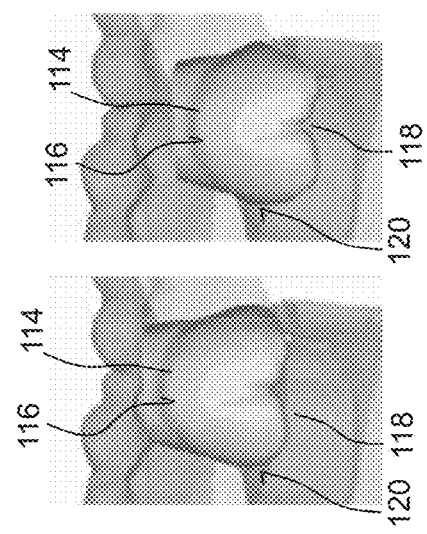
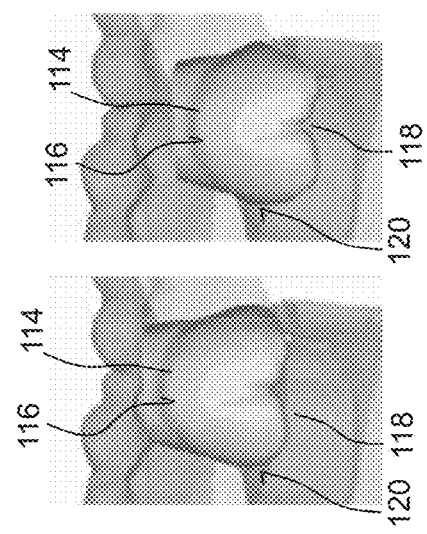

MODELING A PATIENT-INDIVIDUALISED DENTURE PART

The invention relates to a computer-implemented method for modelling a patient-individualised denture part, to a computer program product and also a computer system, and to a processing system for carrying out the method.

Denture parts are usually manufactured by machine or fully by hand. Besides a precise sizing of the denture part, the aesthetics of the denture part, in particular in conjunction with the conditions of the rest of the patient's teeth among which the corresponding denture part is to be arranged, play an important role, and therefore a finishing process by hand is usually provided even in the event that the denture part is produced by machine. Since, in general, no two sets of teeth identical, there are high demands on the modelling of a patient-individualised denture part, which should be adapted precisely both in respect of its dimensions and in respect of its appearance. Even in the case of machine-based production of the denture part, a prior modelling by hand of the corresponding denture part with the use of computer models is therefore usually performed. In this regard, however, known modelling methods have proven to be complex and cumbersome. For example, each individual change to the model must be performed individually by hand. In particular, it may repeatedly be the case that a change to the dental model means that areas of the model already adapted previously no longer fit as a result of the additional change and also have to be adjusted.

DE 10 2011 005899 A1 describes a method for processing, by means of a virtual tool, a first virtual three-dimensional dental model of a denture part produced when planning a denture part. The first virtual dental model is processed by means of the virtual tool, wherein, during the processing by means of the virtual tool, the first virtual dental model is automatically adapted by means of a computer so that certain constraints defined during the planning of the denture are still observed.

US 2018/085203 A1 describes a computer-implemented method for designing a dental restoration on a display, wherein the method comprises providing a virtual three-dimensional representation of at least part of the patient's dental situation. The method comprises displaying a virtual three-dimensional dental restoration model in an alignment with the virtual three-dimensional representation. The method also comprises providing a design tool, which is selectable in order to deform at least part of the three-dimensional dental restoration model. If this design tool is selected, a line may be drawn on a surface of the three-dimensional dental restoration model.

The object of the invention is to enable an improved method for modelling denture parts.

The object forming the basis of the invention is achieved by the features of each of the independent claims. Embodiments of the invention are described in the dependent claims.

Embodiments comprise a computer-implemented method for modelling a patient-individualised denture part, wherein the method comprises:
providing a digital three-dimensional patient situation model, wherein the patient situation model defines patient-specific delimiting surfaces of one or more objects of a set of the patient's teeth which define a patient situation geometry to which the denture part is to be adapted during the course of the modelling,
providing a first digital three-dimensional denture part model in a starting state, wherein the first denture part model defines denture part-specific delimiting surfaces of the denture part which define a denture part geometry,
wherein the first denture part model, in the starting state, has a denture part geometry in the form of a starting geometry,
providing one or more geometric adaptation criteria defined using the patient-specific delimiting surfaces, which criteria must be satisfied by the denture part-specific delimiting surfaces during the course of a patient-individualised adaptation of the denture part geometry to the patient situation geometry,
adapting the denture part geometry of the first denture part model to the patient situation geometry of the patient situation model in a patient-individualised manner,
wherein the patient-individualised adaptation process comprises arranging the first denture part model in a starting position provided by the patient situation model for the denture part,
wherein the patient-individualised adaptation process also comprises repeatedly interactively making user-defined changes to the arranged first denture part model, wherein the first denture part model dynamically passes through a sequence of intermediate states during the course of each of the user-defined changes until a change state resulting from each user-defined change is reached, wherein, for each of the corresponding intermediate states and also the resulting change state, a state-specific state geometry of the first denture part model is automatically calculated from the starting geometry of the first denture part model whilst satisfying the geometric adaptation criteria,
wherein each of the user-defined changes is displayed by means of a graphical user surface on a display device, wherein each display of a user-defined change comprises a display of the first denture part model dynamically passing through the relevant sequence of intermediate states until the corresponding change state has been reached, with the relevant state-specific state geometries calculated for this,
using a change geometry resulting from the patient-individualised adaptation of the first denture part model to provide a patient-individualised denture part geometry for the production of the patient-individualised denture part.

Design models may have the advantage that they allow a user to adapt a digital three-dimensional denture part model, proceeding from a starting state, to the individual conditions of a patient situation geometry. A patient situation geometry is defined by one or more objects arranged in a set of the patient's teeth to which the denture part model is to be adapted. The defined geometric adaptation criteria ensure that each user-defined change is implemented whilst satisfying the corresponding adaptation criteria. In other words, a state which violates a geometric adaptation criterion may thus be prevented from establishing itself as a result of a user-defined change to the denture part model. Embodiments have the advantage of eradicating the need for rectifications on the denture part model, as a result of user-defined changes, in order to once more satisfy the corresponding adaptation criteria. The problem of a user-defined change resulting in the need for a rectification in order to once more satisfy an adaptation criterion that was already satisfied by changes made previously and that has been violated by the new state may thus be avoided. A corresponding rectification may cause the prior user-defined change to be reversed, at least to the extent that it must be repeated in part, which in turn may lead to problems when it comes to satisfying the corresponding adaptation criterion. By fixedly defining the corresponding geometric adaptation criteria, it may be ensured that a time-consuming iterative approximation of a simultaneous satisfaction of the corresponding adaptation criteria on the one hand and user-defined changes to the patient-individualised adaptation of the denture part model on the other hand may be avoided.

Furthermore, displaying a dynamic passing through of a sequence of intermediate states allows a user to better understand the external effects of the user-defined changes defined by him. In particular, the user may therefore identify whether one of the intermediate states passed through dynamically is an advantageous change state of the denture part model sought by the user. If so, the user may arrive at the corresponding intermediate state by reversing part of the user-defined changes. The practicality of the method is thus increased, and the processing time may be significantly reduced.

Here, it is in particular advantageous that the state-specific state geometry is calculated automatically from the starting geometry, both for the individual intermediate states and for the resulting change states. The state geometries of the intermediate states and/or of the change state may thus be calculated separately in each instance from the starting geometry. For example, if a user-defined change is made on the arranged denture part model, the denture part model passes through a sequence of intermediate states. A state-specific state geometry may be calculated for each individual intermediate state of this sequence. Each individual one of these state geometries is calculated from the starting geometry, i.e. in particular without any influence by any previously calculated intermediate states. The individual intermediate states of the sequence, in particular, are not results of steps of an iteration procedure, in which the result of one step is assumed as the starting value of the next step. In other words, in particular, an intermediate state of the sequence is not used as a starting state for calculating the next intermediate state of the sequence. The starting geometry is used each time as the starting state for calculating the intermediate states. If a user-defined change, for example, is reversed and the sequence of intermediate states is passed through in reverse, the intermediate states when passing through the sequence in reverse in particular match exactly with the states when passing forwards through the sequence, since they are each calculated from the starting geometry and the calculations are therefore identical, without encountering any deviations, which may increase over time or with the number of intermediate states passed through and which for example may be caused by numerical effects, such as different rounding errors. For example, a change state, which is likewise calculated from the starting geometry, may thus be independent of the intermediate states passed through, and in particular of numerical effects, such as rounding errors, when calculating these intermediate states. A calculation of the individual state geometries in each case from the starting geometry may ensure that each user-defined change made by the user may be cancelled without difficulty. In particular, an adaptation of the denture part model to an intermediate state passed through beforehand may hereby be facilitated. In particular, a situation in which the user is forced to start the modelling anew since a combination of user-defined changes made by him may no longer be cancelled may thus be avoided. This situation may arise in particular if, in each case from state to state, an adaptation of the denture part model is calculated using numerical approximation methods. For example, as a result of numerical effects, such as rounding errors, it may be that changes are generally unable to be made fully reversible without a fixed reference state of the denture part model. In the present case, a fixed reference state is provided in the form of the starting geometry. Embodiments may thus allow a quicker and much more easily implemented modelling of patient-individualised denture parts.

Embodiments may additionally have the advantage, since the change states are each calculated individually proceeding from the starting geometry, that for each change state a set of change data may be created, which defines the changes made for the corresponding change state as compared to the starting geometry. Such a set of change data makes it possible to transfer any changes made for a first denture part model to a second denture part model in a simple form. For example, for this purpose, the changes defined in the set of change data are applied to the second denture part model. Since these are changes that have been calculated directly from the starting geometry, inaccuracies during the transfer, which inaccuracies may be of a numerical nature and/or specific to the denture part model, may be reduced.

The previously described advantages come into effect in particular if a plurality of denture parts, in particular denture parts which are dependent on one another, are to be modelled.

A denture part is understood to mean any form of object to be arranged in or on a set of patient's teeth in order to replace and/or supplement one or more absent or present natural teeth and/or one or more parts thereof. Denture parts may include, for example, bridges, inlays, overlays, crowns or the like. Denture parts are produced from a denture material, for example from ceramics, such as zinc oxide ceramic, aluminium oxide ceramic, from metals, or metal alloys. For example, CrCo alloys, gold, or gold alloys are used. Furthermore, denture material may also comprise plastic.

A denture part geometry denotes a geometric form and/or forms of a denture part model formed by denture part-specific delimiting surfaces. These forms are able to be quantitatively described by geometric variables or ratios of geometric variables, such as distances, lengths, widths, heights, angles, points, (top) faces, or volumes. A denture part model may be selected from a collection of predefined denture part models, i.e. a library, or may be produced for a specific application. To this end, physical objects of a set of patient's teeth may be used as a template for a digital three-dimensional model, or existing patient-specific digital three-dimensional models may be used as a template and/or starting model.

A patient situation geometry denotes a geometric form and/or forms of a patient situation model or of the models, comprised by the patient situation model, of the corresponding objects of the set of patient's teeth, formed by patient-specific delimiting surfaces of one or more objects of a set of patient's teeth that is/are present and/or is/are to be supplemented. These forms are able to be quantitatively described by geometric variables or ratios of geometric variables, such as distances, lengths, widths, heights, angles, points, (top) faces, or volumes. A patient situation model represents a teeth state and/or a state of one or more parts of a set of patient's teeth in which the denture part is to be fitted or to which it is to be adapted. In this case, the patient situation model is based, for example, on an inspection of a set of patient's teeth and/or one or more parts of a set of patient's teeth.

According to embodiments, the user-defined changes are in each instance displayed simultaneously when they are input. Embodiments may have the advantage that the user is thus provided directly with a visualisation of the adaptations he has made. The intermediate states and the resulting change state are calculated in this case on-the-fly in real time.

According to embodiments, the denture geometry is adapted whilst maintaining morphological features, which are defined by the starting geometry and are characteristic for the denture part. Embodiments may have the advantage that the corresponding denture part always retains its basic functional and/or an aesthetic character.

According to embodiments, providing the resulting change geometry comprises using the resulting change geometry as a patient-individualised denture part geometry. Embodiments may have the advantage that the resulting change geometry may be used for example indirectly as a patient-individualised tooth geometry, for example to produce the denture part by means of a suitable processing method, such as a CAM method or a rapid prototyping method. This may be a material-removing processing method, for example CNC milling, or an additive processing method, for example 3D printing.

According to embodiments, providing the resulting change-geometry comprises transferring the resulting change geometry to a second digital three-dimensional denture part model, wherein the second denture part model has a higher resolution than the first denture part model. Embodiments may have the advantage that they allow a multi-stage modelling of a patient-individualised denture part. The accuracy of the modelled denture part increases here from stage to stage. For example, a first digital three-dimensional denture part model with a first resolution may be used at a first modelling stage. This resolution may be, for example, a comparatively coarse resolution, which allows rapid adaptation of fundamental dimensions of the denture part model to the conditions of a patient situation geometry with low computing effort. The change geometry resulting here may then be transferred to a second denture part model having a higher resolution than the first denture part model. In other words, the user may take advantage of the changes already made. The second denture part model may then be fine-tuned to the corresponding conditions of the patient situation geometry.

According to embodiments, the geometric adaptation criteria define one or more admissible maximum and/or minimum values for positive and/or negative distances or offsets between patient-specific delimiting surfaces of the patient situation model and denture part-specific delimiting surfaces of the denture part model. Embodiments may have the advantage that, due to the geometric adaptation criteria, it may be ensured that each of the calculated state-specific state geometries of the denture part model satisfies one or more basic geometric relationships in respect of patient-specific delimiting faces. A negative distance denotes a distance between a patient-specific delimiting surface and a denture part-specific delimiting surface, wherein the denture part-specific delimiting surface extends inside the patient situation model. A positive distance denotes a distance between a patient-specific delimiting surface and a denture part-specific delimiting surface, wherein the denture part-specific delimiting surface extends outside the patient situation model.

According to embodiments, the patient-specific delimiting faces are delimiting faces of one or more antagonists, comprised by the patient situation model, of one or more approximal teeth comprised by the patient situation model and/or of one or more denture parts comprised by the patient situation model. According to embodiments, one or more of the admissible maximum and/or minimum values is/are zero. Embodiments may have the advantage that a penetration of delimiting faces of the denture part model and the patient situation model may be ruled out in principle.

According to embodiments, the geometric adaptation criteria define one or more admissible minimum values for positive distances between denture part-specific delimiting surfaces of the denture part model. In other words, the geometric adaptation criteria define a minimum material thickness for the denture part model.

According to embodiments, the geometric adaptation criteria defined using the patient-specific delimiting surfaces comprise at least one of the following geometric criteria to be satisfied by the state-specific state geometries calculated during the course of the patient-individualised adaptation of the denture part geometry: material thicknesses of the denture part model limited by the delimiting surfaces do not fall below a predefined first minimum value; maximum penetration depths of delimiting faces of the denture part model and delimiting faces of the patient situation model do not exceed a predefined maximum value; minimum distances between delimiting faces of the denture part model and delimiting faces of the patient situation model do not fall below a predefined second minimum value.

For example, it is specified that a material thickness of the denture part model may not full below a predefined minimum value. Embodiments may have the advantage that a durability and high stability of the denture part may thus be ensured. In particular, it may thus also be ensured that parts of an object of the set of patient's teeth, for example a tooth stump, do not penetrate fully through the denture part model and stick out in part therefrom as a result of a shifting of the denture part model. If a distance between two delimiting faces is reduced as a result of user-defined changes such that said distance corresponds to the predefined first minimum value, a further approaching of the corresponding delimiting faces may thus be prevented. Rather, the distance is kept constant at the corresponding minimum value, and further changes occur as a result of a geometric deformation of the denture part model. Should a user wish, for example, to shift the denture part model within the patient situation geometry, a situation may arise, for example, in which the crown of the denture part model is indeed shifted, however a lower portion of the denture part model remains stationary or areas of delimiting faces of the lower portion remain stationary.

According to embodiments, the delimiting faces of the patient situation model for which the maximum penetration depths or minimum distances are limited are delimiting faces of one or more antagonists, comprised by the patient situation model, of one or more approximal teeth comprised by the patient situation model and/or of one or more denture parts comprised by the patient situation model.

For example, it may be stipulated that maximum penetration depths of delimiting faces of the denture part model and delimiting faces of the patient situation model do not exceed a predefined maximum value. Here, for example, it may be stipulated that no penetration is admissible or, if a corresponding penetration is admissible, said penetration may be limited to an permissible maximum value. A limited penetration between denture part model and patient situation model may be admissible, for example, between the denture part model and an antagonist. Here, a minimum penetration may be expedient in order to be able to ensure that the patient has a sensation of contact when biting and in order to be able to ensure effective chewing. Furthermore, an unlimited penetration during the course of the modelling may be expedient in order to initially adapt the denture part model as a whole to a patient situation geometry and in order to rectify remaining minimum penetrations locally during the course of a fine tuning at the end of the modelling process. This may be achieved, for example, by a local deformation of the surface geometry of the denture part model or by a local removal of material of the denture part model.

For example, it may be stipulated that maximum distances between delimiting faces of the denture part model and delimiting faces of the patient situation model do not exceed a predefined maximum value. Embodiments may have the advantage that it may thus be ensured that distances between denture part model and patient situation model in some sections are not too large.

For example, it may be stipulated that minimum distances between delimiting faces of the denture part model and delimiting faces of the patient situation model do not exceed a predefined minimum value. Embodiments may thus have the advantage that it may be ensured that a distance between denture part model and patient situation model in some sections is not too small.

If a limit value stipulated by one of the adaptation criteria is reached, it may thus be defined, for example, that further user-individual changes of the denture part model by a deformation thereof are allowed on the proviso that the adaptation criteria are satisfied.

Embodiments may have the advantage that a penetration of delimiting faces of the denture part model and the patient situation model may be ruled out in principle.

According to embodiments, the geometric adaptation criteria are structured hierarchically. In the case of geometric adaptation criteria that are incompatible with one another, individual geometric adaptation criteria take precedence in accordance with the hierarchical structure over one or more other geometric adaptation criteria. For example, a plurality of geometric adaptation criteria is stipulated, for example in the form of a preset or by a selection made by the user. A hierarchical structure or order is stipulated for these geometric adaptation criteria, for example in the form of a preset or by a selection made by the user. Should the situation occur that a contradiction results from two or more of the stipulated geometric adaptation criteria, i.e. these geometric adaptation criteria cannot be satisfied at the same time, certain geometric adaptation criteria of the incompatible geometric adaptation criteria take precedence in accordance with the hierarchical structure over other geometric adaptation criteria of the incompatible geometric adaptation criteria. For example, the geometric adaptation criteria are satisfied in order until the further geometric adaptation criteria may no longer be satisfied on account of the one or more contradictions. In this case, for example, the fact that the corresponding further geometric adaptation criteria are not satisfied may be accepted. Alternatively, maximum values stipulated by the corresponding further geometric adaptation criteria may be increased in order, i.e. following the hierarchical order, and/or minimum values stipulated by the corresponding further geometric adaptation criteria may be decreased in order, i.e. following the hierarchical order, until the further geometric adaptation criteria are also satisfied. The maximum values may be increased and the minimum values decreased for example incrementally, for example with predefined increments. Embodiments may have the advantage that conflicts between geometric adaptation criteria may be solved on the basis of the hierarchical structure.

For example, the selection criterion of the keeping of a minimum value for the material thickness may be weighted more highly than the adaptation criterion of a limiting of the penetration depth. For example, in the event of a contradiction between two adaptation criteria, the hierarchically lower adaptation criterion may be given less weight; for example, in the case of a contradiction between minimum material thickness and maximum admissible penetration depth, the maximum admissible penetration depth may thus be given more weight. An adaptation criterion violated as a result of such a conflict is able to be remedied, for example, during the course of a fine tuning of the denture part model at the end of each modelling operation. For example, a desired penetration may thus be removed by a local deformation or material removal at the denture part model.

According to embodiments, the user-defined changes are displayed in real time. Embodiments may have the advantage that a user sees directly what effects user-defined changes have and may adapt these quickly and effectively.

According to embodiments, the user-defined changes each comprise at least one of the following changes defined by an interactive user input: a scaling of an extension of the denture part model in a predefined extension direction of the denture part model; a shift of the denture part model relative to the patient situation model; and a rotation of the denture part model relative to the patient situation model.

According to embodiments, inputting the user-defined changes in each case comprises selecting and interactively processing at least one area of a delimiting surface of the denture part model presented visually on the graphical user surface by means of an interactive digital processing tool provided by the graphical user surface.

According to embodiments, the interactive processing comprises deforming an area and/or trimming a volume portion of the denture part geometry delimited by the area.

A deformation may have the advantage that a general form of the denture part is maintained to the greatest possible extent. Embodiments may have the advantage that local adaptations may be made whilst the general tooth form may remain unchanged. In particular, smooth transitions between different areas of the delimiting surfaces may thus be ensured.

A cutting of a delimiting surface, optionally with an offset, may have the advantage that the denture part is changed only minimally outside the cut area or not at all. For example, what are known as facet faces or ground faces may thus be achieved on teeth. Embodiments may have the advantage that local adaptations of the denture part model are made possible whilst the rest of the geometry may remain unchanged to the greatest possible extent.

By means of a local cutting and/or deforming, contact for example may be optimised, for example approximally and/or occlusally. For example, contact between an occlusal delimiting surface of the denture part model and an occlusal delimiting surface of an antagonist of the denture part comprised by the patient situation model is thus able to be optimised.

According to embodiments, the user-specific changes are input using an input device. The input device, for example, comprises a mouse, a keyboard, a touchpad, a touchscreen, an input pen or stylus, a three-dimensional haptic input device and/or a device for recognising gestures. According to embodiments, the input device is used to control the interactive processing tool on the graphical user surface. According to embodiments, the interactive digital processing tool comprises a cursor for selecting an area of a surface and moving the selected area on the graphical user surface.

The movement may be performed, for example, as a drag-and-drop function. The cursor may be of any design, in particular it may be designed as a tool that symbolises the processing options provided by the cursor or the interactive digital processing tool. According to embodiments, the processing comprises a local application of material, removal of material, smoothing of fissures, and/or deepening of fissures. According to embodiments, a point of the surface is selected. According to embodiments, the area is selected by means of a paintbrush function.

According to embodiments, one or more areas are defined function-specifically in the digital three-dimensional denture part model. Areas comprise, for example, cusps, cusp tips, fissures, chewing faces, etc. According to embodiments, it is predefined for one or more of the areas defined functionally specifically whether these are changeable, for example whether their original form and/or position are to be retained. According to embodiments, the user may define, for example via a user input or hotkeys, whether areas defined functionally specifically are changeable and/or to what extent the corresponding areas are changeable or whether the corresponding areas are unchangeable.

According to embodiments, the user-defined change is input indirectly via hotkeys, numerical values or other 2D control elements, wherein an intermediate algorithm implements a change to the digital three-dimensional denture part model depending on the input. For example, a change may comprise a change to an articular state, a shrinkage, a swelling and/or a tooth ageing or tooth flattening.

According to embodiments, the input of the user-defined changes comprises an adjustment of an adjustable material application value in order to add or remove material virtually in selected areas of the first denture part model, for example a crown or an area of the crown. According to embodiments, the material application value may be positive in the case of a material addition or negative in the case of a material removal.

Embodiments may have the advantage that a material addition and/or material removal may be performed in real time and may be assessed by the user. For example, a necessary layer thickness for a ceramic veneer to be applied to the denture part that is to be produced may be estimated quickly.

A material removal or shrinkage and material addition or swelling technically does not correspond entirely to a scaling. Rather, it is a movement of an area of the surface of the denture part model by a constant distance value relative to a centre of the denture part model over the area, i.e. for each point of the area. In this case the constant distance value is independent of the distance from the centre.

According to embodiments, predefined areas of the denture part model are changed by means of material removal and/or material addition. For example, these areas are aesthetically relevant areas which are to be veneered, for example using ceramic. Aesthetically relevant areas are areas of the denture part model that correspond to areas of the denture part that is to be produced which, when the denture part is arranged in the patient's set of teeth, are routinely visible during the course of normal mouth movements.

According to embodiments, arranging the denture part model in the starting position comprises automatically adapting the denture part model to a preparation margin for the denture part defined in the patient situation model. Embodiments may have the advantage that specified preparation margins are always satisfied by the patient situation model. In particular, it is thus possible to eradicate the need for a rectification to satisfy the preparation margin as a result of a user-defined change to the denture part model. A corresponding preparation margin may defined for example by the user at the start of the process and adapted to patient-individualised conditions of the patient situation model.

According to embodiment the method also comprises the steps of:
choosing a change state of the first denture part model,
simulating a chewing motion for the selected change state of the first denture part model, wherein the simulation of the chewing motion comprises calculating a sequence of relative positions of the denture part model passed through dynamically to an antagonist of the denture part model comprised by the patient situation model, wherein at least one occlusal delimiting face of the denture part model and an occlusal delimiting face of the antagonist are displayed on the display device by means of the graphical user surface for each of the relative positions.

Embodiments may have the advantage that a virtual articulator is provided, by means of which the effects of adaptations of the denture part model to dynamic chewing movements of the patient may be simulated. It may thus be ensured that an adaptation of the denture part is suitable not only for an individual relative positioning with respect to an antagonist, but also for relative positioning during the course of a chewing movement.

According to embodiments, for each of the individual relative positions of the dynamic sequence, areas of the occlusal delimiting face of the denture part model which penetrate the occlusal delimiting face of the antagonist are displayed. According to embodiments, the chewing movement is a generic chewing movement. According to embodiments, the chewing movement is a patient-individualised chewing movement.

During the course of the simulation of the chewing movement, for example the relative position of the antagonist with respect to the denture part is influenced, extended and/or modified. For example, during the course of the simulation, one or more predetermined positions, which are not superimposed, are approached by means of movement paths and at the corresponding predetermined positions are adapted as position of the antagonist. This is the case, for example, if a user uses a slider to choose a jaw movement position calculated beforehand by the virtual articulator and then is provided directly with a display of a result for the corresponding position.

For example, during the course of the simulation, a new virtual antagonist is produced as a superimposition of the many antagonist positions combined by the movement paths and shown in each instance as a virtual imprint in individual movements of the opposing teeth. In this case, a new artificial delimiting face is produced from an envelope of all jaw movement paths.

A virtual articulator denotes a simplified digital simulation of a real articulator, which is a dental apparatus for simulating a chewing movement with standard movement profiles, for example left/right laterotrusion terosion, retrusion, etc. Alternatively, movement paths of the jaw may also be loaded in from measuring systems on the patient and may be used for the movement of the antagonist.

Embodiments may have the advantage that a dynamic interaction between the denture part model and antagonists in the patient situation geometry may be taken into account during the course of the chewing. In particular, the denture part model may thus be adapted to different interaction situations.

According to embodiments, the provided denture part model in the starting state is a generic model for the denture part. Embodiments may have the advantage that generic models may be used which define basic geometric conditions, such as distance ratios between points of the denture part model. During the course of the modelling, a corresponding generic model may be adapted to the conditions of a patient-individualised patient situation model. Here, the generic conditions of the underlying generic model may be retained, for example. Corresponding generic denture part models are provided, for example, in the form of libraries, from which said models may be loaded.

According to embodiments, providing the denture part model in the starting state comprises selecting and copying a tooth and/or tooth part comprised by the patient situation model. According to embodiments, the providing process also comprises a mirroring. Embodiments may have the advantage that, to model a denture part, it is possible to start already from a denture part model which is adapted at least in part to patient-individualised conditions of the patient situation model. A denture part model of this kind which has already been previously adapted may have the advantage that the adaptation process is thus shortened. Embodiments may have the advantage that it is possible to consult existing patient-individualised objects.

According to embodiments, providing the denture part model in the starting state comprises selecting and copying a patient-individualised denture part already adapted to the patient situation model. According to embodiments, the providing process also comprises a mirroring. Embodiments may have the advantage that it is possible to consult existing patient-individualised denture parts.

According to embodiments, the objects of a set of patient's teeth comprise one or more of the following objects: a tooth, a tooth stump, gum, a denture, an implant, a periodontal apparatus, a locator, an occlusal splint, a bar, a dental prosthesis or a partial dental prosthesis, a removable partial denture, a temporary denture, a filling, or an inlay. A periodontal apparatus refers to a functional anchoring system of a tooth also denoted by the term "attachment". A locator refers to a ready-made connection element for connecting a removable denture to an implant.

An occlusal splint refers to a prosthetic-like support which is adapted to the dental arch, in particular is made of plastic, and which is used for example for the treatment of myoarthropathies. A bar is used for example to fasten a bar-retained prosthesis. The bar provides a holding and/or supporting function for holding and/or supporting the bar prosthesis. A bar of this kind may have a round or rectangular cross section, for example. A bar is used to fix at least two teeth or implants, wherein the bar may be secured for example to root caps, anchor crowns or superstructures. For example, a plurality of bars may be interconnected.

According to embodiments, the method also comprises producing the patient-individualised denture part using the change geometry defined as patient-individualised denture part geometry.

According to embodiments, the patient-specific and denture part-specific delimiting surfaces are implemented with use of one of the following methods: a polygonal mesh structure, wherein vertices of the corresponding mesh structure and/or points within the polygons of the mesh structure define the corresponding delimiting surfaces, a point cloud, wherein the points of the point cloud define the corresponding delimiting surfaces, a 3D volume data structure which comprises a voxel grid, or a 3D signed distance field.

According to embodiments, the number and increment of the dynamic sequence is determined depending on a desired target frame rate for the displayed animation or depending on a change that is anticipated visually. It is thus possible to prevent the computer from being loaded unnecessarily and at the same time to ensure the best-possible interactivity. For example, fewer intermediate steps may be calculated in order to accelerate a movement. Conversely, more intermediate steps may be calculated in order to accelerate a movement for a fine-tuning.

Embodiments may have the advantage that, on the one hand, a high degree of interactivity may be ensured, whereas, on the other hand, the computing effort of the computer may be reduced. In addition, by reducing the number of intermediate steps, the dynamic sequence may be passed through more quickly, whereby the denture part model may be adapted more quickly.

According to embodiments, predefined regions of the denture part model are kept outside a boundary. Corresponding boundaries are predefined for example or may be set by the user. Embodiments may have the advantage that a transition region of only limited size may be elastically deformed outside the predefined regions. For example, in order to be able to drag a tooth cusp tip until this is arranged in an appropriate position in the chewing surface of the opposing jaw, the tooth cusp itself does not have to be deformed too significantly if it is a corresponding predefined region.

According to embodiments, denture part models arranged adjacently in the same jaw or in opposite jaws influence one another in order to achieve an optimal dental form. In this case, for example, the upper jaw may have priority over the lower jaw and denture parts to be arranged at the front in the set of teeth may have priority, for aesthetic reasons, over denture parts that are to be arranged further to the rear. For example, mixed forms may be provided, in which the priority is defined as a percentage. Here, it may be defined which of the two mutually influencing denture parts is to have greater priority and which is to have lower priority. Embodiments may have the advantage that, by defining priorities, it is possible to resolve conflicts between mutually influencing adaptations of denture part models.

According to embodiments, one or more denture parts selected by the user are retained on or nestled against a delimiting surface of the patient model, possibly with an offset. For example, contact faces between a denture part and an antagonist may thus be forced at certain positions. At the same time, other denture parts may optionally be brought out of contact with the same delimiting surface, possibly with an offset, for example in order to leave enough space for the cusp tips or fissures of the corresponding denture part relative to the antagonist. Embodiments may have the advantage that different requirements for adaptation to different areas of a denture part model and/or different denture part models may be satisfied.

According to embodiments, boundaries for patient-specific and/or denture part-specific delimiting surfaces may be defined by the user via geometric generated objects. For example, a digital boundary in the form of a plane may be loaded in and placed, for example in the form of a Spee's curve or Wilson's curve. Furthermore, a digital boundary is loaded in for example from a library. For example, a spherical cap is loaded in from a library and placed. A spherical cap is used as a positioning aid for toothless jaws or for preassembled tooth arrangements for the opposite jaw, which may be advantageous for example in the case of a full prosthetic. Embodiments may have the advantage that the modelling may be made more efficient and more effective as a result. In particular, a supplementation of additional elements may be simplified.

According to embodiments, one of the patient-specific delimiting surfaces is defined as a minimum thickness face with respect to a patient-specific delimiting surface, for example of a tooth stump, tooth implant part, and/or tooth abutment part. For example, an offset face on a tooth stump may be defined; a minimum thickness surface may be loaded in or an offset face generated material-specifically may optionally be defined thereon.

According to embodiments, a physically present form is taken into account absolutely and is adapted on-the-fly in the event that the shaping is exceeded. The adaptation is produced for example by cutting and/or under consideration of a predefined morphology, such as a tooth morphology, to an available free space within the physically predefined form. This may be advantageous for example for full prosthetic teeth. According to embodiments, this may be implemented by loading in additional face for each denture part, always moving it together with the denture part or relative to the denture part, and using it as a delimitation of the currently modelled denture part geometry. A corresponding face may be loaded in, for example from a preform library, i.e. for example a library of forms for the use of blanks with prefabricated implant connection, or a full prosthetic tooth library.

Embodiments may have the advantage that pre-forms may also be taken into consideration effectively and efficiently in conjunction with the denture part model. Embodiments may have the advantage that changes may also be implemented effectively and efficiently in the library. In particular, embodiments may ensure that an adaptation that has already been made may be adopted and that there is no need to start again from zero.

According to embodiments, a library may be changed, wherein a first denture part model from a first library is swapped for a second denture part model from a second library. According to embodiments, a current change geometry of the first denture part model is transferred to the second denture part model. This may comprise, for example, a positioning and form of the first denture part model, for example position of cusps, fissures, or other contact points. Embodiments may have the advantage that not all adaptations have to be performed again in the event that the library is changed.

According to embodiments, a plurality of denture part models from different libraries are shown for the same denture part by means of the graphical user surface. Embodiments may have the advantage that denture part models may be shown simultaneously for the same denture part and may also be moved or changed on-the-fly. An adaptation and display may be implemented either by split-screen display or simultaneously in the form of a superimposition, for example transparently and/or with different colours.

Embodiments may have the advantage that different libraries may be taken into account simultaneously. This makes it possible to perform one and the same adaptation for a number of libraries at the same time, so that identical adaptation results for different libraries may be produced at the end and a selection can be made from these. In particular, an adaptation may thus be made which is not only optimised for one library, but for a number of and/or all libraries at the same time.

According to embodiments, the denture part is a bridge which for example is loaded from a bridge library. Embodiments may have the advantage that a relative position and/or size of individual teeth or a plurality of teeth comprised by the bridge may be fixedly predefined. This may be advantageous for example for a full prosthetic of back teeth. According to embodiments, these molar teeth are loaded in together and are fixedly defined relative to one another in respect of size and position. According to embodiments, entire tooth bridges are stored jointly as one surface.

Embodiments may have the advantage that, in the case of bridges and/or bridge parts, an adaptation may be simplified and accelerated since these bridges and/or bridge parts are provided and adapted as an object or a denture part model.

According to embodiments, the denture part model, which is loaded for example from a library, comprises a gingiva component. Embodiments may have the advantage that a gingiva component is also contained directly in the denture part model and for example may also be deformed and/or moved in the event of a change to a tooth form of the denture part model. According to embodiments, the denture part model with gingiva component is a bridge model, which is loaded for example from a bridge library.

According to embodiments, a digital gingiva component is generated automatically, for example on-the-fly, for a given denture part model. For example, a gingiva component is produced where there is too great a distance between approximal delimiting faces or where there is too great a distance from a patient's jaw. Embodiments may have the advantage that gaps in the gums may be prevented or automatically filled. Embodiments may have the advantage that a gingiva component may also be taken into account effectively and efficiently during the adaptation of denture part models.

According to embodiments, transformations and deformations of front teeth are implemented symmetrically. For example, transformations and deformations are mirrored symmetrically. Embodiments may have the advantage that a symmetrical adaptation may be implemented for front teeth.

According to embodiments, the method comprises a simulation of a tooth ageing or quasi-abrasion. With increasing degree of ageing, fissures for example become increasingly larger, tooth cusps are lowered increasingly and/or chewing surfaces are flattened increasingly. The degree of ageing may be input for example as a user-defined change by means of an adjustable value. A heuristically simulated tooth ageing process may thus be controlled, for example on-the-fly. Embodiments may have the advantage that ageing processes may be taken into account effectively and efficiently during the course of the modelling.

Embodiments may also comprise a computer program product for modelling a patient-individualised denture part, which computer program product comprises a nonvolatile, computer-readable storage medium with computer-readable program instructions for modelling the patient-individualised denture part, wherein execution of the program instructions by a processor of a computer system prompts the computer system to perform a method for modelling the patient-individualised denture part, which method comprises:

provides a digital three-dimensional patient situation model, wherein the patient situation model defines patient-specific delimiting surfaces of one or more objects of a set of the patient's teeth which define a patient situation geometry to which the denture part is to be adapted during the course of the modelling, providing a digital three-dimensional denture part model in a starting state, wherein the denture part model defines denture part-specific delimiting surfaces of the denture part which define a denture part geometry, wherein the denture part model, in the starting state, has a denture part geometry in the form of a starting geometry, providing one or more geometric adaptation criteria defined using the patient-specific delimiting surfaces, which criteria must be satisfied by the denture part-specific delimiting surfaces during the course of a patient-individualised adaptation of the denture part geometry to the patient situation geometry, adapting the denture part geometry of the denture part model to the patient situation geometry of the patient situation model in a patient-individualised manner, wherein the patient-individualised adaptation process comprises arranging the denture part model in a starting position provided by the patient situation model for the denture part, wherein the patient-individualised adaptation process also comprises repeatedly interactively making user-defined changes to the arranged denture part model, wherein the denture part model dynamically passes through a sequence of intermediate states during the course of each of the user-defined changes until a change state resulting from each user-defined change is reached, wherein, for each of the corresponding intermediate states and also the resulting change state, a state-specific state geometry of the denture part model is automatically calculated from the starting geometry of the denture part model whilst satisfying the geometric adaptation criteria, wherein each of the user-defined changes is displayed by means of a graphical user surface on a display device, wherein each display of a user-defined change comprises a display of the denture part model dynamically passing through the relevant sequence of intermediate states until the corresponding change state has been reached, with the relevant state-specific state geometries calculated for this, defining a change geometry, resulting from the patient-individualised adaptation of the denture part model, as patient-individualised denture part geometry to be used to produce the patient-individualised denture part.

According to embodiments, the computer program product is configured to execute one or more of the aforementioned embodiments of the method for modelling a patient-individualised denture part.

Embodiments also comprise a computer system for modelling a patient-individualised denture part, wherein the computer system comprises a storage medium, a processor, an input device and a display device, wherein computer-readable program instructions for modelling the patient-individualised denture part are stored on the storage medium, wherein execution of the program instructions by the processor of the computer system prompts the computer system to perform a method for modelling the patient-individualised denture part, which method comprises:

providing a digital three-dimensional patient situation model, wherein the patient situation model defines patient-specific delimiting surfaces of one or more objects of a set of the patient's teeth which define a patient situation geometry to which the denture part is to be adapted during the course of the modelling, providing a digital three-dimensional denture part model in a starting state, wherein the denture part model defines denture part-specific delimiting surfaces of the denture part which define a denture part geometry, wherein the denture part model, in the starting state, has a denture part geometry in the form of a starting geometry, providing one or more geometric adaptation criteria defined using the patient-specific delimiting surfaces, which criteria must be satisfied by the denture part-specific delimiting surfaces during the course of a patient-individualised adaptation of the denture part geometry to the patient situation geometry, adapting the denture part geometry of the denture part model to the patient situation geometry of the patient situation model in a patient-individualised manner, wherein the patient-individualised adaptation process comprises arranging the denture part model in a starting position provided by the patient situation model for the denture part, wherein the patient-individualised adaptation process also comprises repeatedly interactively making user-defined changes to the arranged denture part model, wherein the denture part model dynamically passes through a sequence of intermediate states during the course of each of the user-defined changes until a change state resulting from each user-defined change is reached, wherein, for each of the corresponding intermediate states and also the resulting change state, a state-specific state geometry of the denture part model is automatically calculated from the starting geometry of the denture part model whilst satisfying the geometric adaptation criteria, wherein each of the user-defined changes is displayed by means of a graphical user surface on a display device, wherein each display of a user-defined change comprises a display of the denture part model dynamically passing through the relevant sequence of intermediate states until the corresponding change state has been reached, with the relevant state-specific state geometries calculated for this, defining a change geometry, resulting from the patient-individualised adaptation of the denture part model, as patient-individualised denture part geometry to be used to produce the patient-individualised denture part.

According to embodiments, the computer system is configured to execute one or more of the aforementioned embodiments of the method for modelling a patient-individualised denture part.

Embodiments also comprise a processing system for producing a patient-individualised denture part, wherein the processing system comprises a computer system according to one of the aforementioned embodiments and also a processing device for producing the patient-individualised denture part from denture material with use of the patient-individualised denture part geometry.

Figure 2:
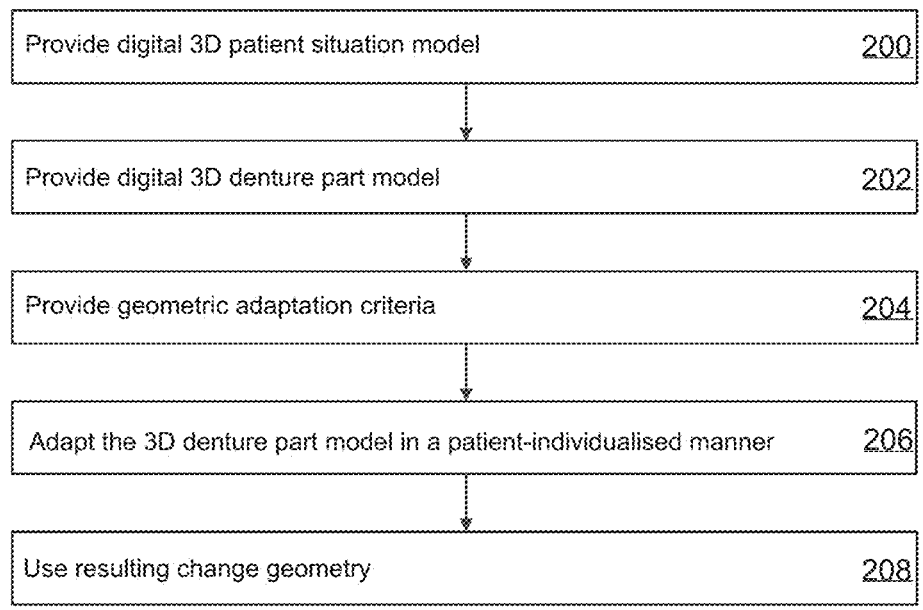
Figure 3:
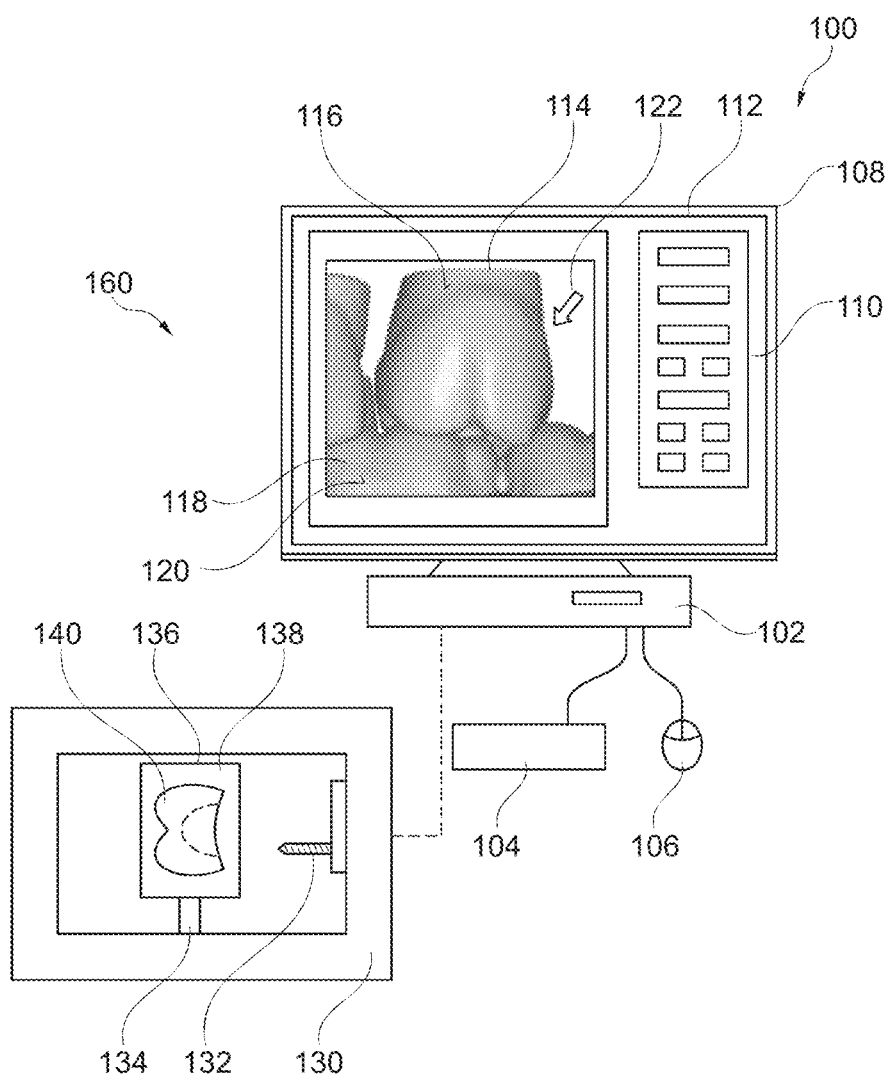
Figure 4:
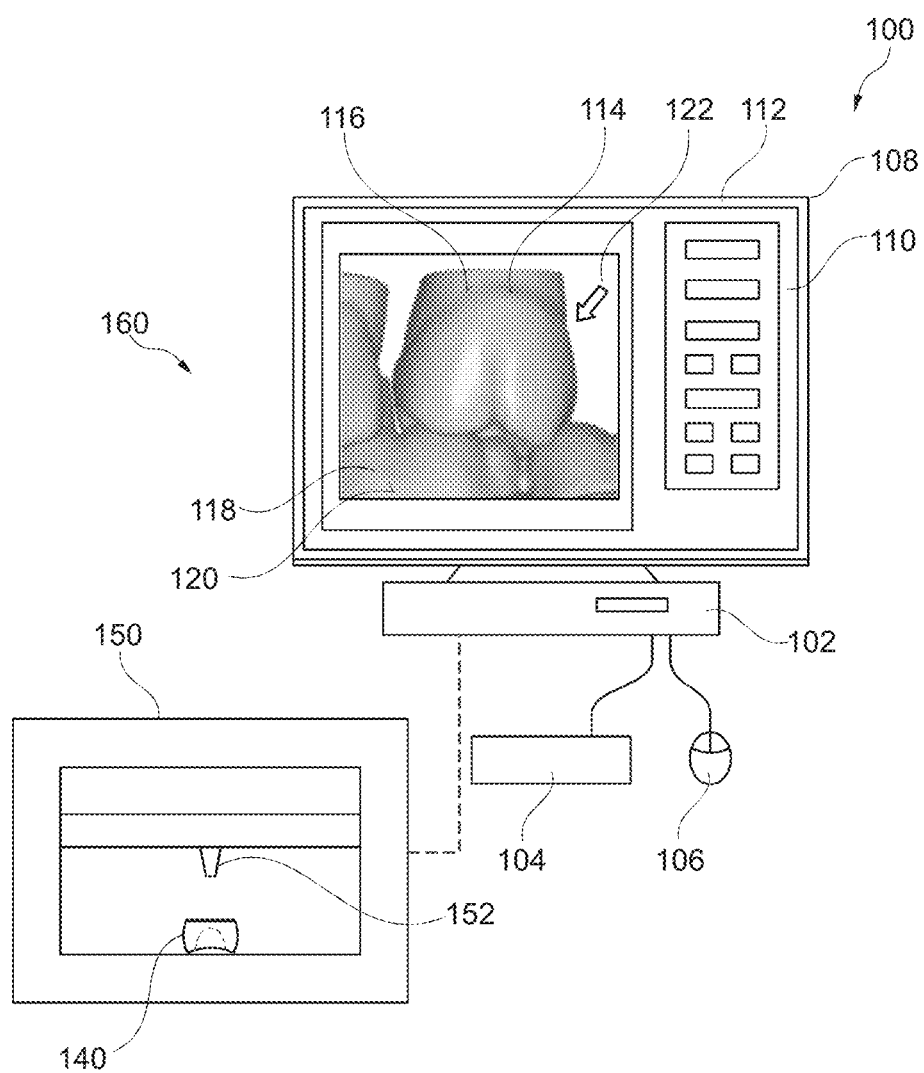
Figure 5A:
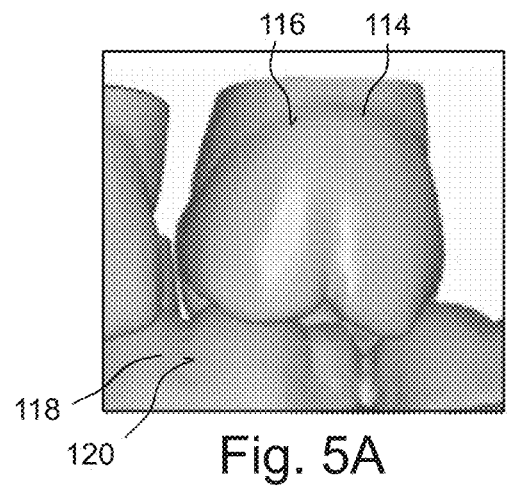
Figure 5B:
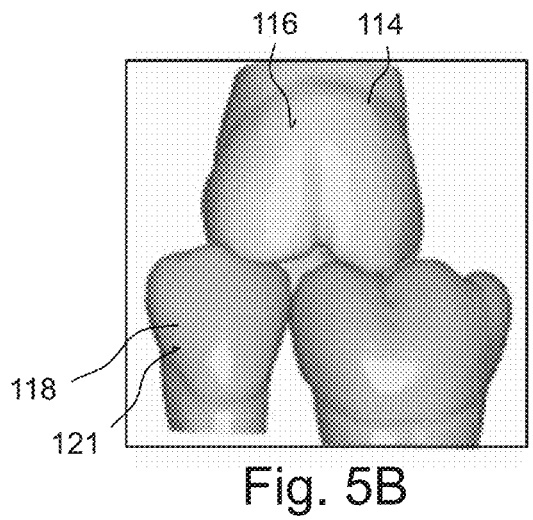
Figure 5C:
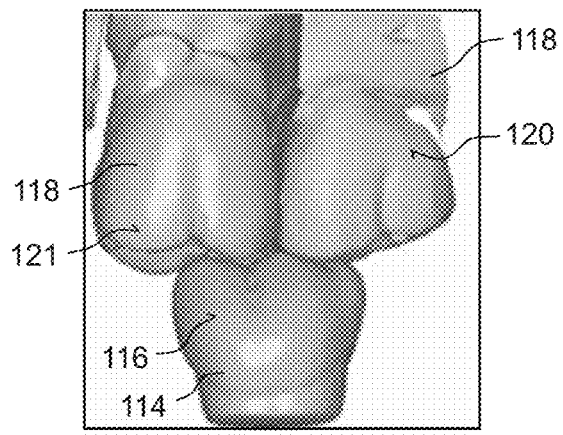
Figure 6A:
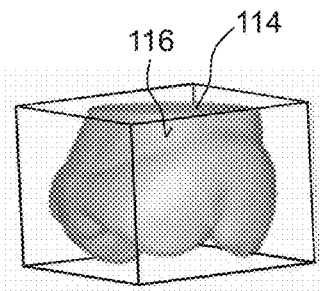
Figure 6B:
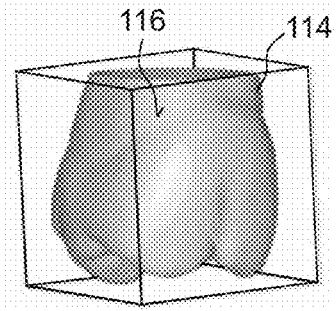
Figure 6C:
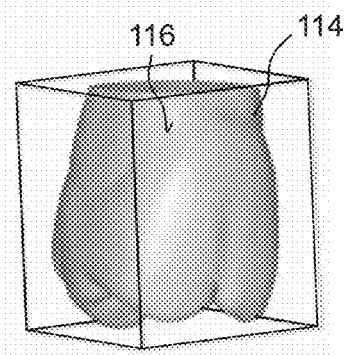
Figure 7E:
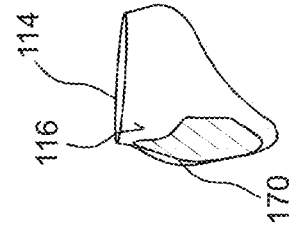
Figure 7D:
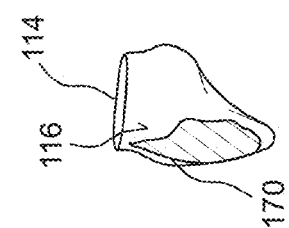
Figure 7C:
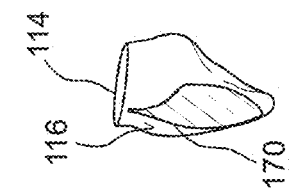
Figure 7B:
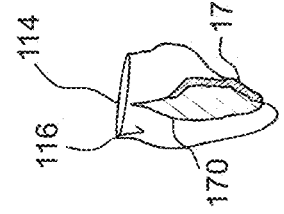
Figure 7A:
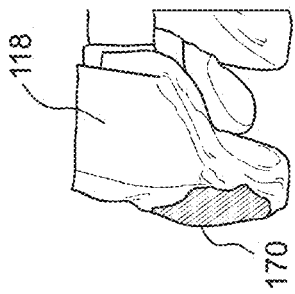
Figure 8E:
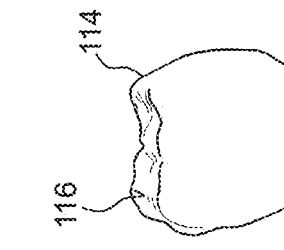
Figure 8D:
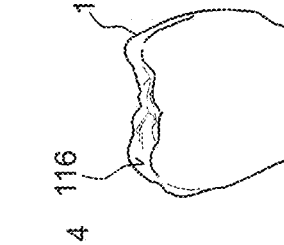
Figure 8C:
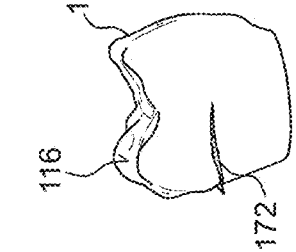
Figure 8B:
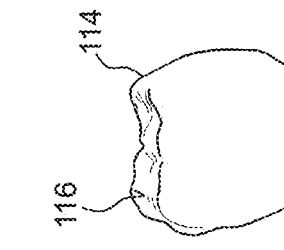
Figure 8A:
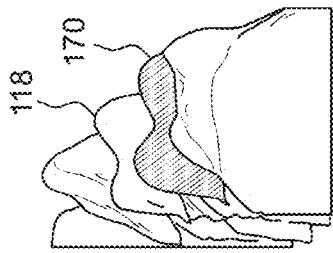
Figure 11A:
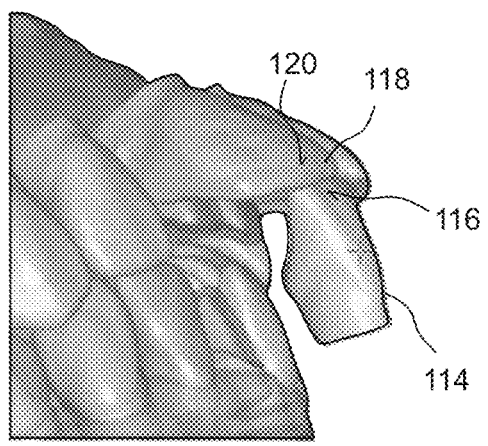
Figure 11B:
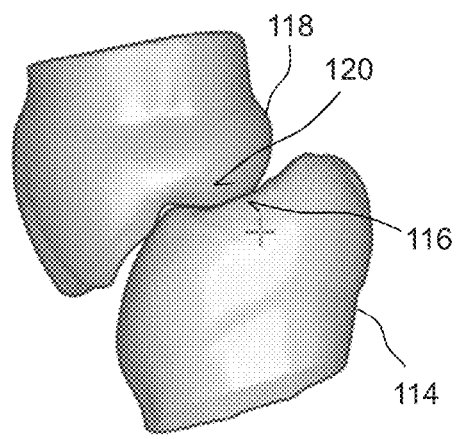
Figure 11C:
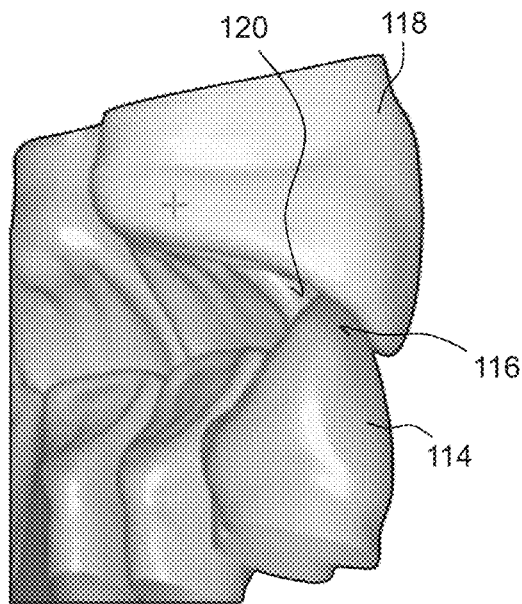
Figure 12:
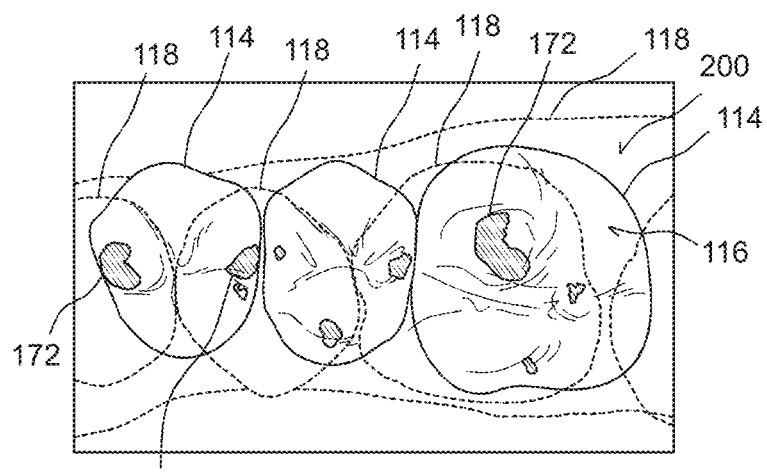
Figure 13A:
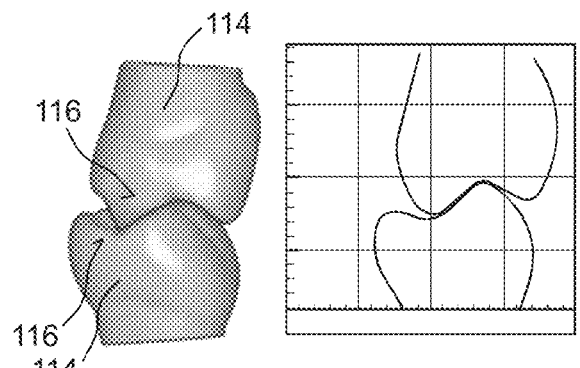
Figure 13B:
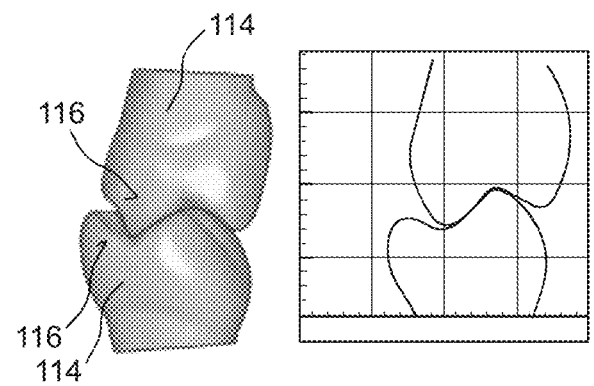
Figure 13C:
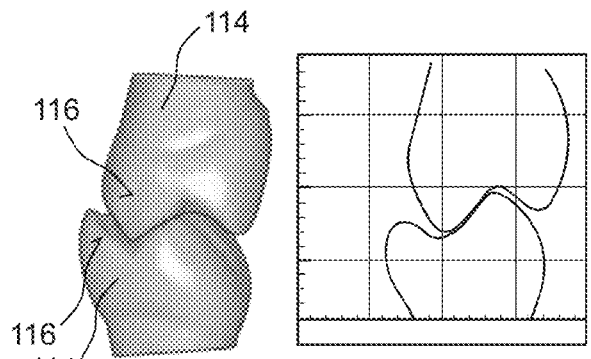
Figure 14A:
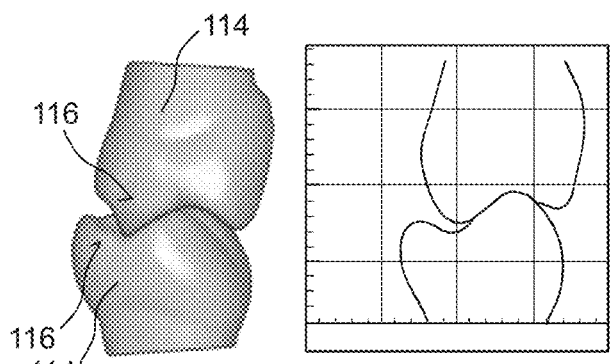
Figure 14B:
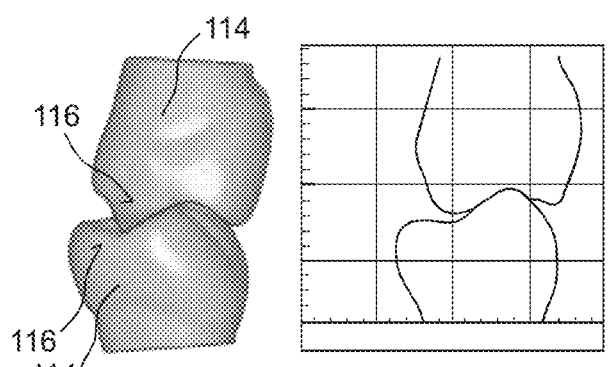
Figure 14C:
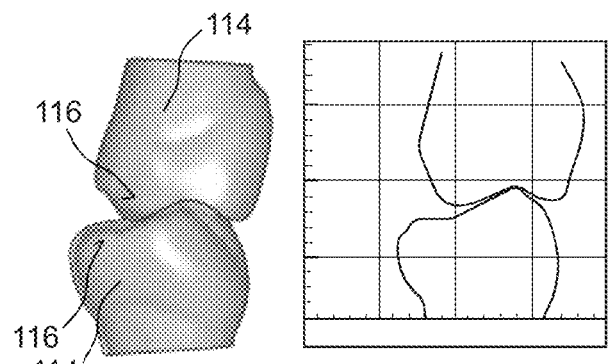
Figure 15A:
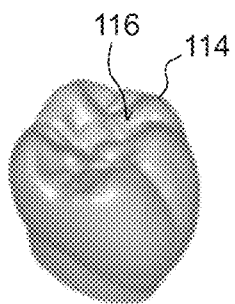
Figure 16A:
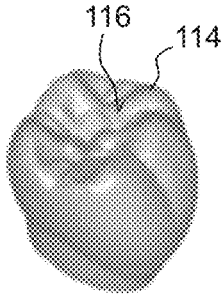
Figure 15B:
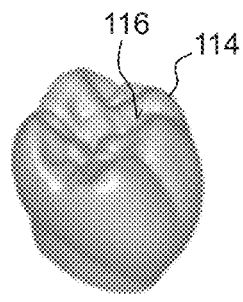
Figure 16B:
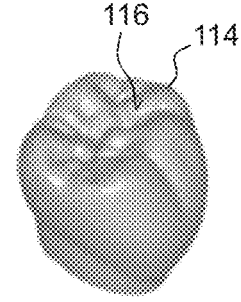
Figure 15C:
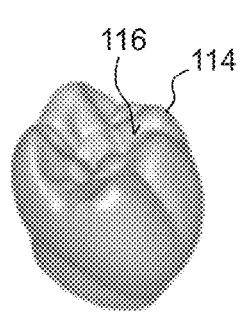
Figure 16C:
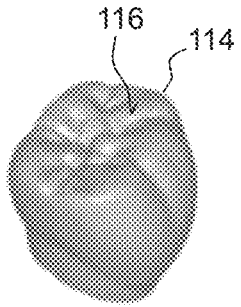
Figure 17A:
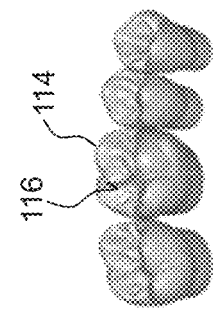
Figure 17B:
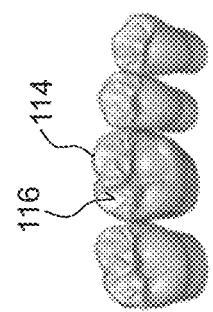
Figure 17C:
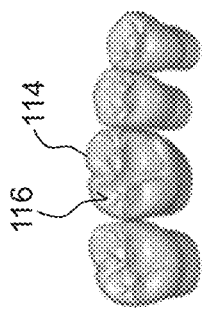
Figure 18A:
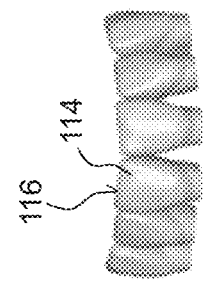
Figure 18B:
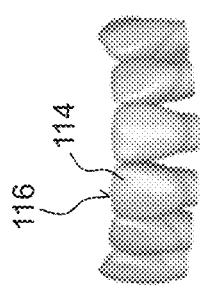
Figure 18C:
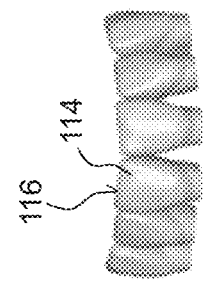

Embodiments of the invention will be explained hereinafter in greater detail with reference to the drawings, in which:

FIG. 1 shows a schematic block diagram of an exemplary computer system for modelling a patient-individualised denture part, FIG. 2 shows a schematic flow diagram of an exemplary method for modelling a patient-individualised denture part, FIG. 3 shows a schematic block diagram of an exemplary processing system for modelling a patient-individualised denture part, FIG. 4 shows a schematic block diagram of an exemplary processing system for modelling a patient-individualised denture part, FIGS. 5A-C show exemplary denture part models and patient situation models, FIGS. 6A-C show exemplary adaptations of a denture part model, FIGS. 7A-E show an exemplary adaptation of a denture part model, FIGS. 8A-E show an exemplary adaptation of a denture part model, FIGS. 9A-D show an exemplary adaptation of a denture part model, FIGS. 10A-D show an exemplary adaptation of a denture part model, FIGS. 11A-C show exemplary adaptations of denture part models and patient situation models, FIG. 12 shows an exemplary penetration situation of denture part models and patient situation models, FIGS. 13A-C show an exemplary quasi-abrasion of denture part models, FIGS. 14A-C show an exemplary quasi-abrasion of denture part models, FIGS. 15A-C show an exemplary quasi-abrasion of a denture part model, FIGS. 16A-C show an exemplary quasi-abrasion of a denture part model, FIGS. 17A-C show an exemplary quasi-abrasion of denture part models, and FIGS. 18A-C show an exemplary quasi-abrasion of denture part models.

Elements of the following embodiments which correspond to one another are denoted by the same reference signs.

FIG. 1 shows a schematic block diagram of a computer system 100 for modelling a patient-individualised denture part. The computer system 100 comprises a hardware component 102 with one or more processors and one or more storage media. Computer-readable program instructions for modelling the patient-individualised denture part are stored on one or more of the storage media. An execution of the program instructions by one or more of the processors of the hardware component 102 prompts the computer system 100 to perform a method for modelling the patient-individualised denture part. The computer system 100 also comprises a display device 108 for displaying a graphical user surface 110. The computer system 100 also comprises input devices, such as a keyboard 104 and a mouse 106, for making an interactive user input. The graphical user surface 110 comprises control elements 112, which may be used with use of the input devices 104, 106 to choose a modelling of a digital three-dimensional denture part model 114. A digital three-dimensional denture part model 114 is also shown on the graphical user surface 110 and the user may adapt said model in a patient-individualised manner, using the input devices 104, 106, to a patient situation model 118 likewise provided on the graphical user surface. The denture part model 114 is defined by denture part-specific delimiting surfaces 116 which define a denture part geometry. By means of its patient-specific delimiting surfaces 120, the patient situation model 118 defines a patient situation geometry. The patient-specific delimiting surfaces 120 of the patient situation model are delimiting surfaces of one or more objects of a set of patient's teeth. Furthermore, the graphical user surface comprises, for example, a digital processing tool 122, which allows the user, by means of the input devices 104, 106, to select and to process or to change in a user-defined manner the denture part model 114 and/or areas of the denture part model 114 that is to be adapted in a patient-individualised manner. Corresponding user-defined changes comprise, for example, a shift, rotation and/or scaling of the denture part model 114. The computer-readable program instructions also define geometric adaptation criteria for the user-defined changing of the denture part model 114, which criteria must be satisfied. In other words, only changes that satisfy the predefined geometric adaptation criteria are admissible. If the denture part model is changed by the user with use of the input devices 104, 106, for example is shifted relative to the patient situation model, the corresponding change is shown on the user surface 110 as a dynamic sequence of intermediate states of the denture part model 114 which said model passes through until a change state corresponding to the input user-defined changes is reached. In other words, the user may shift, rotate and/or scale the denture part model for example within the graphical user surface 110 relative to the patient situation model 120, wherein the corresponding changes are shown in real time as dynamic image sequences.

FIG. 2 shows a schematic flow diagram of an exemplary method for modelling a patient-individualised denture part. A digital three-dimensional patient situation model is provided in block 200. The patient situation model defines patient-specific delimiting surfaces of one or more objects of a set of patient's teeth. In other words, the patient situation model reflects a starting situation in the patient's set of teeth, to which model the denture part is to be adapted during the course of the modelling.

The patient-specific delimiting surfaces define a patient situation geometry or area structure. The patient situation model or the delimiting surfaces are described for example by means of a polygonal mesh structure, for example by means of triangles, by means of a point cloud, by means of a 3D volume data structure, or by means of a 3D signed distance field. The patient situation model is produced for example by measuring the patient's set of teeth or objects of the patient's set of teeth directly in the patient's mouth or indirectly by measuring at least one impression or model of the patient's set of teeth or objects of the patient's set of teeth, for example made of plaster or plastic. For example, X-ray images, tomosynthesis images, and/or computed tomography images may be used in the measurement. Furthermore, the patient situation model may comprise one or more already-modelled digital three-dimensional denture part models, i.e. objects which are already fixedly defined for use in or on a patient's set of teeth and likewise must be taken into account when adapting the denture part during the course of the modelling.

A digital three-dimensional denture part model is provided in a starting state in block 202. Similarly to the patient situation model, the denture part model is also defined via delimiting surfaces, i.e. denture part-specific delimiting surfaces. These delimiting surfaces describe a denture part geometry. The denture part model or the delimiting surfaces are described for example by means of a polygonal mesh structure, for example by means of triangles, by means of a point cloud, by means of a 3D volume data structure, or by means of a 3D signed distance field. The denture part model may be, for example, a generic model, for example a tooth, which is loaded from a library, a copy of an object comprises by the patient situation model, a copy of an already adapted patient-individualised denture part model, or a partially adapted patient-individualised denture part model. The denture part model, in the starting state, has a denture part geometry in the form of a starting geometry.

One or more geometric adaptation criteria defined using the patient-specific delimiting surfaces are defined in block 204. These adaptation criteria must be satisfied by the denture part-specific delimiting surfaces during the course of a patient-individualised adaptation of the denture part geometry to the patient situation geometry. In other words, only adaptations of the denture part geometry which satisfy the adaptation criteria are allowed, or user-defined changes for adapting the denture part geometry are implemented such that these satisfy the adaptation criteria. The adaptation criteria define for example an admissible maximum and/or minimum positive and/or negative distance or offset between a patient-specific delimiting surface and a denture part-specific delimiting surface. Furthermore, the adaptation criteria for example define an admissible material minimum thickness, i.e. an admissible minimum offset between two denture part-specific delimiting surfaces. If a user makes a defined change, for example shifts the denture part model relative to the patient situation model, such that an adaptation criterion would be violated, for example since a denture part-specific delimiting surface would penetrate a patient-specific delimiting surface and an admissible maximum negative offset would be exceeded, the change is thus only implemented to such an extent that it is compatible with the adaptation criterion. In the event of the shift, this for example would cause such denture part-specific delimiting surfaces which have reached a maximum shift state relative to a patient-specific delimiting surface admissible in accordance with the adaptation criteria to no longer be able to be shifted any further relative to the corresponding patient-specific delimiting surface. Denture part-specific delimiting surfaces which do not conflict with the adaptation criteria, for example the admissible maximum shift state has not yet been reached, may be shifted further, which leads to a deformation of the denture part geometry. Here, the deformation is, for example, such that basic geometric relationships of the denture part geometry, i.e. characteristic properties of the form of the denture part, are retained to the greatest possible extent. Basic geometric relationships of the denture part geometry may comprise, for example, distance ratios, curvature ratios, etc. The adaptation criteria for example may be predefined and/or may be set by the user. A deformation of the denture part geometry may be calculated for example with use of a Laplace deformation process.

In block 206 the denture part geometry of the denture part model is adapted in a patient-individualised manner to the patient situation geometry of the patient situation model. To this end, the denture part model is arranged in a starting position provided by the patient situation model for the denture part. Furthermore, interactive user-defined changes are made repeatedly on the arranged denture part model. These changes for example comprise a scaling of an extension of the denture part model along a predefined direction of extension of the denture part model, a shifting of the denture part model relative to the patient situation model and/or a rotation of the denture part model relative to the patient situation model. For example, at least one area of a delimiting surface of the denture part model reproduced visually on the graphical user surface is processed selectively and interactively by means of an interactive digital processing tool provided by the graphical user surface.

In this case the denture part model dynamically passes through a sequence of intermediate states during the course of each of the user-defined changes until a change state resulting from each user-defined change is reached. For each of the corresponding intermediate states and also the resulting change state, a state-specific state geometry of the denture part model is automatically calculated in the corresponding intermediate state from the starting geometry of the first denture part model whilst satisfying the geometric adaptation criteria. Each of the user-defined changes is displayed on a display device by means of a graphical user surface. The user-defined changes are each displayed for example simultaneously to their input. The display of each of the user-defined changes in each instance comprises a display of the denture part model dynamically passing through the relevant sequence of intermediate states until the corresponding change state has been reached, with the relevant state-specific state geometries calculated for this. The number and increment of the intermediate states comprises by the dynamic sequence may be predefined and/or set by the user. According to embodiments, it may be adapted automatically depending on the available computing power of the computer system.

In block 208 a change geometry resulting from the patient-individualised adaptation of the first denture part model is used to provide a patient-individualised denture part geometry for the production of the patient-individualised denture part. For example, the resulting change geometry is used as patient-individualised denture part geometry for the denture part that is to be produced. To this end, for example in response to an output command of the user to output the constructed denture part, a digital data set comprising patient-individualised denture part geometry is generated for automatedly producing the physical denture part, a denture part semifinished product, or a prototype of the denture part from denture material, for example tooth restoration material. For example, the automated production is implemented by means of CAM or rapid prototyping methods, such as CNC milling or 3D printing. A denture part semifinished product is a semifinished product that has a denture-like form and from which the denture part is produced by further subsequent, for example manual processing steps.

According to alternative embodiments, providing the resulting change geometry comprises transferring this resulting change geometry to a second digital three-dimensional denture part model of the same denture part. This second denture part model has a higher resolution than the first denture part model. The previously described method may then be repeated for this second denture part model, wherein the starting state of the second denture part model is defined either by a generic starting state, i.e. independently of the adopted change geometry, or by the adopted change geometry. The expression "independently of the adopted change geometry" in this instance means that the adopted change geometry is treated as a first user-defined change.

FIG. 3 shows a schematic block diagram of a processing system 160 for producing a patient-individualised denture part. The processing system 160 comprises a computer system 100 for modelling a patient-individualised denture part according to FIG. 1. The computer-readable program instructions of the computer system 100 are also configured to produce a processing device 130 for producing the patient-individualised denture part 140 from denture material or tooth restoration material 138 of a blank 136. For the production, for example, a patient-individualised denture part geometry is used, which is the result of the modelling of the patient-individualised denture part using the computer 100. The corresponding denture part geometry is provided for example as a series production model and the computer system 100 controls the processing device 130, which for example is a CAM processing device, according to the patient-individualised denture part geometry. Here, the processing device 130 is actuated for example such that a denture part 140 is worked out from the blank 136 with a processing tool 132 using a material-removing processing method, the geometry of said denture part corresponding to the patient-individualised denture part geometry. To this end, the processing device 130 provides the blank 136, which is held by a holding device 134.

FIG. 4 shows a schematic block diagram of an alternative processing system 160, which besides a computer system 100, which corresponds to the computer system 100 from FIG. 1, also comprises a 3D printer 150 as a processing device for producing the patient-individualised denture part 140 from denture material using the patient-individualised denture part geometry provided by the computer system 100. The 3D printer 150 comprises a print element 152, with which the denture material is output in layers, so that the patient-individualised denture part 140 is created in layers in accordance with the patient-individualised denture part geometry.

FIGS. 5A to 5C show different types of patient situation models 118 which are used for the modelling of the patient-individualised denture part. FIG. 5A shows a situation in which the patient situation model 118 is based on a scan of one or more objects of a set of patient's teeth. The patient situation model 118 is defined by the scanned patient-specific delimiting surfaces 120. These may be directly scanned delimiting surfaces 120 of the corresponding objects or a scan of a negative impression or positive impression of the actual objects of the patient's set of teeth. A digital three-dimensional denture part model 114 is adapted to this patient situation model 118 and is defined by delimiting surfaces 116. FIG. 5B shows a situation in which the objects of the patient's set of teeth are already-modelled digital three-dimensional denture part models with modelled delimiting surfaces 121, which form the patient situation model 118 and to which the denture part model 114 is adapted. FIG. 5C lastly shows a patient situation model 118 which is defined from a combination of scanned patient-specific delimiting surfaces 120 and modelled delimiting surfaces 121 of a three-dimensional denture part model modelled for the patient's set of teeth. The digital three-dimensional denture part model 114 is adapted in a patient-individualised manner to this patient situation model 118.

FIGS. 6A to 6C show an exemplary user-defined change to a denture part model 114 which defines denture part-specific delimiting surfaces 116. The exemplary user-defined change is a scaling in which an opposite side of the denture part geometry is kept constant. The scaling is, for example, along a main axis of the tooth, which for example may be an occlusal axis, a mesial axis or a buccal axis. FIG. 6B shows a starting situation of the denture part geometry; FIG. 6A shows a scaling of the corresponding denture part geometries reduced along the occlusal axis, whereas FIG. 6C shows a scaling of the denture part geometries enlarged along the occlusal axis.

FIGS. 7A to 7E show an incremental deformation of a denture part model 114 for a front tooth under consideration of an adaptation criterion in the form of a predetermined minimum thickness. The minimum thickness is presented by the boundary 170, which the denture part-specific delimiting surfaces 116, in this case the buccal delimiting face, must not exceed. If the denture part model 114 is arranged on the boundary 170, the boundary may, for example, protrude from the denture part model 114 in a rear region which is not comprised by the buccal delimiting face. The region 172 of the boundary 170 would thus penetrate the denture part model 114. If the front tooth or the denture part model 114 of the front tooth is shifted in the lingual direction, this would lead to a deformation of the front tooth, with the diameter increasing in the lingual direction since the buccal delimiting face of the denture part model 114 may not exceed the specified boundary 170. The boundary 170 is in this case noticeably completely surrounded. A corresponding situation is shown in FIGS. 8A to 8E for a back tooth, i.e. a premolar or molar. Again, the minimum thickness is defined by a boundary 170, which in this case has the form of a tooth. If the denture part model 114 is shifted in the occlusal direction, the occlusal face as delimiting surface 116 must not penetrate the predefined boundary 170 in accordance with the adaptation criterion, whereby the cusps are flattened and the denture part model 114 is stretched in the occlusal direction. A region 172 of the boundary 170 may firstly penetrate the denture part model 114 below the occlusal face. If, however, the denture part model 114 is shifted downwards in the occlusal direction until the occlusal face comes into the region of the boundary 170, the occlusal face is shifted above the boundary 170 and the penetrations 172 disappear. FIGS. 7B to 7E and 8B to 8E additionally each illustrate a dynamic sequence which is passed through during the course of a user-defined change to the change geometry of the denture part models 114 shown in FIGS. 7E and 8E respectively.

FIGS. 9A to 9D show an adaptation of a denture part model 114 for a front tooth to an antagonist comprised by a patient situation model 118 under consideration of an adaptation criterion in accordance with which no penetration is allowed between the denture part model 114 to be adapted and the antagonist of the patient situation model 118. In this case, as is already the case in FIGS. 7A to 7E, the diameter of the front tooth is increased in the lingual direction, wherein at the same time the buccal delimiting face of the denture part model 114 remains practically unchanged. FIGS. 9A to 9B illustrate a dynamic sequence which is passed through during the course of a user-defined change to the change geometry of the denture part model 114 shown in FIG. 9E.

FIGS. 10A to 10D show an adaptation of a denture part model 114 for a back tooth under the same adaptation criterion as already provided in FIGS. 9A to 9D, in accordance with which a penetration of the denture part model 114 and of an antagonist of a patient situation model 118 is prohibited. In this case, the occlusal face is partially stretched in the occlusal direction, wherein the denture part model 114 extends around the antagonist. FIGS. 9A to 9B illustrate a dynamic sequence which is passed through during the course of a user-defined change to the change geometry of the denture part model 114 shown in FIG. 9E.

FIG. 11A shows an adaptation of a denture part model 114, in which the corresponding denture part model 114 remains undeformed and an adaptation criterion, for example an exclusion of a penetration with an antagonist of a patient situation model 118, is compensated for by the corresponding antagonist. Accordingly, the antagonist is rotated here from its original position. FIG. 11B shows an example in which the adaptation criterion is satisfied both by the denture part model 114 and by an antagonist of the patient situation model 118, in which both are deformed. FIG. 11O shows an example in which the adaptation criterion is satisfied exclusively by a deformation of the denture part model 114 that is to be adapted, whereas the patient situation model 118 remains unchanged.

FIG. 12 shows penetrations 172 of an occlusal delimiting surface 116 of a denture part model 114 with an occlusal delimiting face 120 of a patient situation model 118, in this case of an antagonist. The corresponding regions in which a penetration 172 is present may be removed, for example by cutting the corresponding regions 172 of the denture part model 114 or by locally deforming the occlusal delimiting face 116 of the denture part model 114 in these regions 172. FIG. 12 shows penetrations 172 for a relative positioning of denture part models 114 and patient situation models 118. In the case of a virtual articulator, for example corresponding representations are shown for a plurality of different positionings of denture part model 114 and patient situation model 118 together with any penetrations 172. The different positionings correspond here to different relative positionings which are passed through during the course of a chewing movement. The penetrations 172 possibly present may be shown in succession in the form of a dynamic sequence, in which the different positionings are passed through in succession. The user may thus check for each positioning in succession whether adaptations are necessary on account of any penetrations 172 present and may perform these adaptations as applicable. Alternatively, a superimposition of the penetrations 172 may be projected onto the denture part model 114 for the different positioning. The user may thus look and check whether adaptations are necessary on account of penetrations 172 and may perform these adaptations as applicable. When making an adaptation in this case, the user may consider all penetrations 172 for all positionings at the same time on account of the superimposition.

FIGS. 13A to 13C show an implementation of a quasi-abrasion, in which the cervical limits are retained and the occlusions between the antagonists formed by the two denture models 116 are substantially retained. The left part of FIGS. 13A to 13C in each instance shows the denture models 116 with their delimiting surfaces 118; the right hand side in each instance shows a cross section through the denture models 116. In FIG. 13A, through FIG. 13B to FIG. 13C, in the shown example the abrasion decreases, i.e. the relative heights of the cusps and bottoms of the fissures of the occlusal faces increase.

FIGS. 14A to 14C show an implementation of a quasi-abrasion, in which the abrasion increases starting from FIG. 14A, which is identical to FIG. 13A, through FIG. 14B to FIG. 14C. During the course of the increase in the abrasion, the height of the cusps or the bottom of the fissures in the occlusal face decreases. As beforehand in the case of FIGS. 13A to 13C, the cervical limits are fixed and the occlusion remains practically unchanged.

FIGS. 15A to 15C show, similarly to FIGS. 13A to 13C before, a decrease in a quasi-abrasion, which corresponds more to younger teeth, whereas FIGS. 16A to 16C show an increase of a quasi-abrasion for a denture part model 114 with its delimiting surfaces 116, by means of which an ageing process of the teeth may be remedied. FIGS. 16A to 16C correspond here to FIGS. 14A to 14C. In the case of a virtual ageing of this kind of the denture part model 114, the starting geometry is deformed algorithmically so that it satisfies certain properties which are typically encountered in the teeth of older patients. These properties for example comprise flatter fissures and/or greater smoothing of the anatomical structures of the tooth surface.

FIGS. 17A to 17C show a corresponding quasi-abrasion for a plurality of denture part models 114 for back teeth, wherein FIG. 17B shows a starting situation, relative to which the abrasion decreases in FIG. 17A, whereas it increases relatively in FIG. 17C.

FIGS. 18A to 18C show a corresponding quasi-abrasion for a plurality of denture part models 114 for front teeth, in which a corresponding ageing process is shown, in particular by a smoothing of the incisal delimiting surfaces 116 or of the incisal edge comprised thereby. Again, FIG. 18B shows a starting situation, relative to which the quasi-abrasion decreases in FIG. 18A, whereas it increases relatively in FIG. 18C.

LIST OF REFERENCE SIGNS

100 Computer system
102 Hardware component
104 Input device
106 Input device
108 Display device
110 Graphical user surface
112 Control elements
114 Denture part model
116 Delimiting surfaces
118 Patient situation model
120 Delimiting surfaces
121 Delimiting surfaces
122 Digital processing tool
130 Processing device
132 Processing tool
134 Holding device
136 Blank
138 Denture material
140 Denture part
150 3D printer
152 Print element
160 Processing system
170 Boundary
172 Penetration region

The invention claimed is:

1. A computer-implemented method for modelling a patient-individualised denture part wherein the method comprises:
providing a digital three-dimensional patient situation model, wherein the patient situation model defines patient-specific delimiting surfaces of one or more objects of a set of a patient's teeth which define a patient situation geometry to which the denture part is to be adapted during the course of the modelling,
providing a first digital three-dimensional denture part model in a starting state, wherein the first denture part model defines denture part-specific delimiting surfaces of the denture part which define a denture part geometry,
wherein the first denture part model, in the starting state, has a denture part geometry in the form of a starting geometry,
providing one or more geometric adaptation criteria defined using the patient-specific delimiting surfaces, which criteria must be satisfied by the denture part-specific delimiting surfaces during the course of a patient-individualised adaptation of the denture part geometry to the patient situation geometry,
adapting the denture part geometry of the first denture part model to the patient situation geometry of the patient situation model in a patient-individualised manner,
wherein the patient-individualised adaptation process comprises arranging the first denture part model in a starting position provided by the patient situation model for the denture part, wherein the patient-individualised adaptation process also comprises repeatedly interactively making user-defined changes to the arranged first denture part model, wherein the first denture part model dynamically passes through a sequence of intermediate states during the course of each of the user-defined changes until a change state resulting from each user-defined change is reached, wherein, for each of the corresponding intermediate states and also the resulting change state, a state-specific state geometry of the first denture part model is automatically calculated from the starting geometry of the first denture part model whilst satisfying the geometric adaptation criteria, wherein each of the user-defined changes is displayed by means of a graphical user surface on a display device, wherein each display of a user-defined change comprises a display of the first denture part model dynamically passing through the relevant sequence of intermediate states until the corresponding change state has been reached, with the relevant state-specific state geometries calculated for this, using a change geometry resulting from the patient-individualised adaptation of the first denture part model to provide a patient-individualised denture part geometry for the production of the patient-individualised denture part.

2. The method according to claim 1, wherein providing the resulting change geometry comprises using the resulting change geometry as a patient-individualised denture part geometry.

3. The method according to claim 1, wherein providing the resulting change-geometry comprises transferring the resulting change geometry to a second digital three-dimensional denture part model, wherein the second denture part model has a higher resolution than the first denture part model.

4. The method according to claim 1, wherein the geometric adaptation criteria define one or more admissible maximum and/or minimum values for positive and/or negative distances between patient-specific delimiting surfaces of the patient situation model and denture part-specific delimiting surfaces of the denture part model.

5. The method according to claim 1, wherein the geometric adaptation criteria define one or more admissible minimum values for positive distances between denture part-specific delimiting surfaces of the denture part model.

6. The method according to according to claim 1, wherein the geometric adaptation criteria are structured hierarchically, and, in the event of incompatible geometric adaptation criteria, individual geometric adaptation criteria are given priority over one or more other geometric adaptation criteria in accordance with the hierarchical structure.

7. The method according to claim 1, wherein the user-defined changes are displayed in real time.

8. The method according to claim 1, wherein the user-defined changes each comprise at least one of the following changes defined by an interactive user input: a scaling of an extension of the denture part model in a predefined extension direction of the denture part model; a shift of the denture part model relative to the patient situation model; and a rotation of the denture part model relative to the patient situation model.

9. The method according to claim 1, wherein inputting the user-defined changes in each case comprises selecting and interactively processing at least one area of a delimiting surface of the denture part model presented visually on the graphical user surface by means of an interactive digital processing tool provided by the graphical user surface.

10. The method according to claim 9, wherein the interactive processing comprises deforming an area and/or trimming a volume portion of the denture part geometry delimited by the area.

11. The method according to claim 1, wherein arranging the denture part model in the starting position comprises automatically adapting the denture part model to a preparation margin for the denture part defined in the patient situation model.

12. The method according to claim 1, wherein the method also comprises:
choosing a change state of the first denture part model,
simulating a chewing motion for the selected change state of the first denture part model, wherein the simulation of the chewing motion comprises calculating a sequence of relative positions of the denture part model passed through dynamically to an antagonist of the denture part model comprised by the patient situation model, wherein at least one occlusal delimiting face of the denture part model and an occlusal delimiting face of the antagonist are displayed on the display device by means of the graphical user surface for each of the relative positions.

13. The method according to claim 12, wherein, for each of the individual relative positions of the dynamic sequence, areas of the occlusal delimiting face of the denture part model which penetrate the occlusal delimiting face of the antagonist are displayed.

14. The method according to claim 1, wherein the provided denture part model in the starting state is a generic model for the denture part.

15. The method according to claim 1, wherein the objects of a set of the patient's teeth comprise one or more of the following objects: a tooth, a tooth stump, gum, a denture, an implant, a periodontal apparatus, a locator, an occlusal splint, a bar, a dental prosthesis or a partial dental prosthesis, a removable partial denture, a temporary denture, a filling, or an inlay.

16. The method according to claim 1, wherein the method also comprises producing the patient-individualised denture part using the change geometry defined as patient-individualised denture part geometry.

17. The method according to claim 1, wherein the patient-specific and denture part-specific delimiting surfaces are implemented with use of one of the following methods: a polygonal mesh structure, wherein vertices of the corresponding mesh structure and/or points within the polygons of the mesh structure define the corresponding delimiting surfaces, a point cloud, wherein the points of the point cloud define the corresponding delimiting surfaces, a 3D volume data structure which comprises a voxel grid, or a 3D signed distance field.

18. A computer program product for modelling a patient-individualised denture part, which computer program product comprises a non-volatile, non-transitory computer-readable storage medium with computer-readable program instructions for modelling the patient-individualised denture part, wherein execution of the program instructions by a processor of a computer system prompts the computer system to perform a method for modelling the patient-individualised denture part, which method comprises:
providing a digital three-dimensional patient situation model, wherein the patient situation model defines patient-specific delimiting surfaces of one or more objects of a set of a patient's teeth which define a patient situation geometry to which the denture part is to be adapted during the course of the modelling, providing a digital three-dimensional denture part model in a starting state, wherein the denture part model defines denture part-specific delimiting surfaces of the denture part which define a denture part geometry, wherein the denture part model, in the starting state, has a denture part geometry in the form of a starting geometry, providing one or more geometric adaptation criteria defined using the patient-specific delimiting surfaces, which criteria must be satisfied by the denture part-specific delimiting surfaces during the course of a patient-individualised adaptation of the denture part geometry to the patient situation geometry, adapting the denture part geometry of the denture part model to the patient situation geometry of the patient situation model in a patient-individualised manner,
 wherein the patient-individualised adaptation process comprises arranging the denture part model in a starting position provided by the patient situation model for the denture part,
 wherein the patient-individualised adaptation process also comprises repeatedly interactively making user-defined changes to the arranged denture part model, wherein the denture part model dynamically passes through a sequence of intermediate states during the course of each of the user-defined changes until a change state resulting from each user-defined change is reached, wherein, for each of the corresponding intermediate states and also the resulting change state, a state-specific state geometry of the denture part model is automatically calculated from the starting geometry of the denture part model whilst satisfying the geometric adaptation criteria,
 wherein each of the user-defined changes is displayed by means of a graphical user surface on the display device, wherein each display of a user-defined change comprises a display of the denture part model dynamically passing through the relevant sequence of intermediate states until the corresponding change state has been reached, with the relevant state-specific state geometries calculated for this, defining a change geometry, resulting from the patient-individualised adaptation of the denture part model, as patient-individualised denture part geometry to be used to produce the patient-individualised denture part.

19. A computer system for modelling a patient-individualised denture part, wherein the computer system comprises a storage medium, a processor, an input device and a display device, wherein computer-readable program instructions for modelling the patient-individualised denture part are stored on the storage medium, wherein execution of the program instructions by the processor of the computer system prompts the computer system to perform a method for modelling the patient-individualised denture part, which method comprises:

providing a digital three-dimensional patient situation model, wherein the patient situation model defines patient-specific delimiting surfaces of one or more objects of a set of a patient's teeth which define a patient situation geometry to which the denture part is to be adapted during the course of the modelling, providing a digital three-dimensional denture part model in a starting state, wherein the denture part model defines denture part-specific delimiting surfaces of the denture part which define a denture part geometry, wherein the denture part model, in the starting state, has a denture part geometry in the form of a starting geometry, providing one or more geometric adaptation criteria defined using the patient-specific delimiting surfaces, which criteria must be satisfied by the denture part-specific delimiting surfaces during the course of a patient-individualised adaptation of the denture part geometry to the patient situation geometry, adapting the denture part geometry of the denture part model to the patient situation geometry of the patient situation model in a patient-individualised manner,
 wherein the patient-individualised adaptation process comprises arranging the denture part model in a starting position provided by the patient situation model for the denture part,
 wherein the patient-individualised adaptation process also comprises repeatedly interactively making user-defined changes to the arranged denture part model, wherein the denture part model dynamically passes through a sequence of intermediate states during the course of each of the user-defined changes until a change state resulting from each user-defined change is reached, wherein, for each of the corresponding intermediate states and also the resulting change state, a state-specific state geometry of the denture part model is automatically calculated from the starting geometry of the denture part model whilst satisfying the geometric adaptation criteria,
 wherein each of the user-defined changes is displayed by means of a graphical user surface on the display device, wherein each display of a user-defined change comprises a display of the denture part model dynamically passing through the relevant sequence of intermediate states until the corresponding change state has been reached, with the relevant state-specific state geometries calculated for this, defining a change geometry, resulting from the patient-individualised adaptation of the denture part model, as patient-individualised denture part geometry to be used to produce the patient-individualised denture part.

20. A processing system for producing a patient-individualised denture part, wherein the processing system comprises a computer system according to claim 19 and a processing device for producing the patient-individualised denture part from denture material with use of the patient-individualised denture part geometry.

* * * * *